US006586358B2

(12) United States Patent
Llatas et al.

(10) Patent No.: US 6,586,358 B2
(45) Date of Patent: Jul. 1, 2003

(54) BIDENTATE DIIMINE NICKEL AND PALLADIUM COMPLEXES AND POLYMERIZATION CATALYSTS OBTAINED THEREFROM

(75) Inventors: Luis Mendez Llatas, Mostoles (ES); Antonio Muñoz-Escalona Lafuente, Madrid (ES); Juan Campora Perez, Sevilla (ES); Ernesto Carmona Guzman, Sevilla (ES); Manuel Lopez Reyes, Sevilla (ES)

(73) Assignee: Repsol Quimica, S.A., Madrid (ES)

( * ) Notice: Subject to any disclaimer, the term of this patent is extended or adjusted under 35 U.S.C. 154(b) by 80 days.

(21) Appl. No.: 09/804,505

(22) Filed: Mar. 12, 2001

(65) Prior Publication Data

US 2002/0010352 A1 Jan. 24, 2002

(30) Foreign Application Priority Data

Mar. 13, 2000 (EP) .............................................. 00500041

(51) Int. Cl.$^7$ .......................... B01J 31/00; B01J 37/00; C08F 4/02; C08F 4/60
(52) U.S. Cl. ...................... 502/167; 502/117; 502/104; 502/155
(58) Field of Search ................................ 502/104, 117, 502/155, 167

(56) References Cited

U.S. PATENT DOCUMENTS

| | | | | | |
|---|---|---|---|---|---|
| 3,624,000 A | * | 11/1971 | Throckmorton | ......... | 252/429 B |
| 3,668,146 A | * | 6/1972 | Ruhle | .......................... | 252/428 |
| 3,803,090 A | * | 4/1974 | Reinisch et al. | ......... | 260/46.5 E |
| 3,844,974 A | * | 10/1974 | Throckmorton | .......... | 252/429 B |
| 6,309,997 B1 | * | 10/2001 | Fujita et al. | ................ | 502/167 |
| 6,399,724 B1 | * | 6/2002 | Matsui et al. | ............... | 502/117 |
| 6,403,738 B1 | * | 6/2002 | Johnson et al. | ............. | 502/167 |
| 6,410,768 B1 | * | 6/2002 | Llatas et al. | ................ | 502/155 |

FOREIGN PATENT DOCUMENTS

| WO | WO 96/23010 | 8/1996 |
|---|---|---|
| WO | WO 97/48736 | 12/1997 |
| WO | WO 98/27124 | 6/1998 |
| WO | WO 98/30612 | 7/1998 |
| WO | WO 98/56832 | 12/1998 |
| WO | WO 99/12981 | 3/1999 |

OTHER PUBLICATIONS

US 2002/0010352 A1, US Pre–Grant publication to Llatas et al., published Jan. 2002.*

* cited by examiner

Primary Examiner—Mark L. Bell
Assistant Examiner—J. Pasterczyk
(74) Attorney, Agent, or Firm—Ladas & Parry

(57) ABSTRACT

The present invention relates to a bidenitate diimino-complex of nickel or palladium containing at least one group $OSi(R)_3$ wherein each R, equal to or different from each other, is selected from the group consisting of: $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl, and $C_8$–$C_{20}$ alkenylaryl, linear or branched, preferably each R is independently methyl, ethyl or propyl. The present invention also relates to the process for the preparation of bidentate diimino complexes of nickel and palladium as well as the process for their use in olefin polymerization.

15 Claims, No Drawings

BIDENTATE DIIMINE NICKEL AND PALLADIUM COMPLEXES AND POLYMERIZATION CATALYSTS OBTAINED THEREFROM

FIELD OF THE INVENTION

This invention relates to a new class of nickel and palladium complexes useful in the (co)polymerization of olefins.

BACKGROUND OF THE INVENTION

It has been recently discovered that complexes of nickel or palladium with alpha-diimine ligand can be used as catalysts for polymerizing olefins; for instance WO 96/23010 discloses with several examples various types of these complexes, showing that they can be used for polymerizing a large number of olefins.

Immobilizing these complexes on solid supports to enable heterogeneous polymerization processes, such as those based on gas-phase, bulk or slurry processes, is important for their efficient industrial utilization. In particular, some non supported nickel catalysts give rise to polymers characterized by a high level of branching. The melting points of these polymers are anticipated to be as low as to present problems with reactor operation at typical industrial operating temperatures, especially when heat dissipation by solvents is unavailable, as in continuous gas phase polymerization.

WO 96/23010 discloses supported diimine palladium or nickel catalysts. It exemplifies a process wherein a complex activated with a cocatalyst is adsorbed on silica.

WO 97/48736 relates to immobilized catalysts; they are substantially obtained by preparing a precursor solution mixing together the complex with an aluminoxane and adding this precursor solution to a porous support.

In some examples of WO 98/56832 the cocatalyst was supported on an inorganic support and then a diimino-complex was added, then the obtained catalyst was prepolymerized.

For avoiding the drawback of the migration of the active species into the homogeneous phase during the polymerization reaction, a chemical bond between the carrier and the diimino-complex could be desirable.

An object of the present invention is a bidentate diimino-complex of nickel or palladium containing a siloxy group, that can be easily supported on a carrier through a chemical bond between the carrier and the complex itself.

Another object of the present invention is an olefin polymerization catalyst comprising as catalyst component a diimino-complex of nickel or palladium containing a siloxy group.

A further object of the present invention is a solid polymerization catalyst comprising the diimino-complex of nickel or palladium object of the present invention, a carrier and a cocatalyst.

In this solid catalyst, the catalytic centres are attached to the support by means of the alkoxysilane functionality, thus providing a true heterogeneous catalyst. The preparation of said catalyst precursor results in little or no contaminating secondary reaction products, hence the catalyst is substantially or completely free from undesirable impurities. The catalysts can be used in solution, high pressure, slurry or gas-phase processes. The catalysts are especially useful for the production of branched polyethylene without requiring co-monomer.

SUMMARY OF THE INVENTION

The present invention relates to a bidentate diimino-complex of nickel or palladium containing at least one group $OSi(R)_3$ wherein each R, equal to or different from each other, is selected from the group consisting of: $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl, and $C_8$–$C_{20}$ alkenylaryl, linear or branched, preferably each R is independently methyl, ethyl or propyl.

The present invention also relates to the process for the preparation of bidentate diimino complexes of nickel and palladium as well as the process for their use in olefin polymerization.

DETAILED DESCRIPTION OF THE INVENTION

The present invention relates to a bidentate diimino-complex of nickel or palladium containing at least one group $OSi(R)_3$ wherein each R, equal to or different from each other, is selected from the group consisting of: $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$, alkylaryl, $C_8$–$C_{20}$ arylalkenyl, and $C_8$–$C_{20}$ alkenylaryl, linear or branched, preferably R is methyl, ethyl or propyl. Preferably the bidenitate diimino-complex of nickel and palladium is defined by the following general formulas:

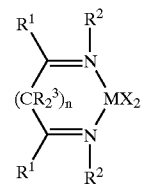

I

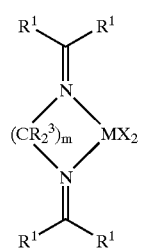

II wherein

M is nickel or palladium, n is 0, 1, 2 or 3; m is 1, 2 or 3, each X, equal to or different from each other, is independently selected from the group consisting of: halogen, hydrogen, OR, $N(R)_2$, R, wherein each R is independently selected from the group consisting of: $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl, and $C_8$–$C_{20}$ alkenylaryl; linear or branched, preferably each R is independently methyl, ethyl or propyl; two X taken together can also form an aromatic or aliphatic divalent ligand, containing two equal or different donor atoms belonging to the group 14–16 of the periodic table of the elements, such as catecholate, 1,2-ethanediolate or 1,2-phenylenediamide, α-deprotonated-β-diketone, α-deprotonated-β-ketoester such as acetylacetonate or hexafluoracetylacetonate;

each $R^1$, equal to or different from each other, is selected from the group consisting of: hydrogen, a monovalent aliphatic or aromatic hydrocarbon group, optionally containing heteroatoms of group 14 to 16 of the periodic table of the elements or boron; with the proviso that at least one $R^1$ group is represented by the formula: $R^4OSi(R)_3$;

wherein each $R^4$, equal to or different from each other, is a divalent aliphatic or aromatic hydrocarbon group containing from 1 to 20 carbon atoms, optionally containing from 1 to 5 heteroatoms of groups 14 to 16 of the periodic table of the elements and/or boron;

preferably it is $CR^5_2(R^6)_aCR^5_2$, wherein each $R^5$, equal to or different from each other, is selected from the group consisting of: hydrogen and R; two $R^5$ can also unite to form a ring;

$R^6$ is a divalent radical selected from the group comprising: O, NR, S, $SiR^5_2$, $C_1-C_{20}$ alkylidene, $C_3-C_{20}$ cycloalkylidene, $C_2-C_{20}$ alkenylidene, $C_6-C_{20}$ arylidene, $C_7-C_{20}$ alkylarylidene, $C_7-C_{20}$ arylalkylidene, $C_8-C_{20}$ arylalkenylidene, or $C_8-C_{20}$ alkenylarylidene, linear or branched, optionally containing heteroatoms of group 14 to 16 of the periodic table of the elements, and/or boron;

a is 0 or 1;

each $R^2$, equal to or different from each other, is a radical which contains from 1 to 20 carbon atoms; this group optionally contains heteroatoms of group 14 to 16 of the periodic table of the elements and boron;

preferably each $R^2$ is independently selected from the group consisting of: $C_1-C_{20}$ alkyl, $C_3-C_{20}$ cycloalkyl, $C_6-C_{20}$ aryl, $C_2-C_{20}$ alkenyl, $C_7-C_{20}$ arylalkyl, $C_7-C_{20}$ alkylaryl, $C_8-C_{20}$ arylalkenyl, $C_8-C_{20}$ alkenylaryl, linear or branched, optionally substituted by $BR^5_2$, $OR^5$, $SiR^5_3$, or $NR^5_2$, most preferably $R^2$ is a alkylsubstituted phenyl, naphthyl or anthracyl, most preferably $R^2$ is a 2,6 dialkylphenyl group, optionally substituted in position 4 by a group R as defined above.

each $R^3$, equal to or different from each other, is hydrogen or a radical which contains from 1 to 20 carbon atoms; this group optionally contains heteroatoms of group 14 to 16 of the periodic table of the elements and/or boron;

preferably $R^3$ is independently selected from the group consisting of: hydrogen, $C_1-C_{20}$ alkyl, $C_3-C_{20}$ cycloalkyl, $C_6-C_{20}$ aryl, $C_2-C_{20}$ alkenyl, $C_7-C_{20}$ arylalkyl, $C_7-C_{20}$ alkylaryl, $C_8-C_{20}$ arylalkenyl, and $C_8-C_{20}$ alkenylaryl, linear or branched, optionally substituted by $BR^5_2$, $OR^5$, $SiR^5_3$, or $NR^5_2$ where $R^5$ is defined above;

two or more $R^1$, $R^2$, $R^3$ and $R^4$ can also unite to form a from 4 to 15 membered aliphatic or aromatic ring; the ring optionally contains heteroatoms of group 14 to 16 of the periodic table of the elements and boron.

Preferably $R^1$ is selected from the group consisting of: hydrogen; $C_1-C_{20}$ alkyl; $C_3-C_{20}$ cycloalkyl; $C_6-C_{20}$ aryl; $C_2-C_{20}$ alkenyl; $C_7-C_{20}$ arylalkyl; $C_7-C_{20}$ alkylaryl; $C_8-C_{20}$ arylalkenyl; and $C_8-C_{20}$ alkenylaryl; linear or branched, optionally substituted by $BR^5_2$, $OR^5$, $SiR^5_3$, $NR^5_2$; or $R^4OSi(R)_3$ where $R^4$ and $R^5$ are defined above;

examples of group $CR^5_2(R^6)_aCR^5_2$ $OSi(R)_3$ are:

—$CH_2$—$CH_2$—$OSiMe_3$; —$CH_2$—$(CH_2)_p$—$CH_2$—$OSiMe_3$ wherein p ranges from 1 to 10;

—$CH_2$—O—$CH_2$—$OSiMe_3$; —$CH_2$—$C_6H_4$—$CH_2$—$OSiMe_3$; —$CH(Et)$—$CH_2$—$OSi(Et)_2Me$;

—$CH_2$—$CH_2$—O—$CH_2OSi(iPr)_3$; —$CH_2$—$Si(CH_3)_2$—$CH_2OSi(iPr)_3$;

—$CH_2$—$CH_2$—$Si(CH_3)_2$—$CH_2OSi(iPr)_3$; —$CH_2$—$CH_2$—$CH_2$—$N(CH_3)$—$CH_2$—$CH_2$—$CH_2OSi(iPr)_3$;

—$C(Me)_2$—$CH_2$—$C_6H_4$—$CH_2$—$CH_2$—$OSi(C_5H_{11})_3$; —$CH_2$—$CH_2$—$C_6H_4$—$C_6H_4O$—$CH_2$—$CH_2$—$OSi(CH_2Ph)_3$;

—$C(CH_3)_2$—$C(CH_3)_2$—$OSi(C_6H_4Me)_3$; —$CH(Me)$—$CH(Me)$—$OSi(Et)(Me)_2$.

Compounds of general formula I and II, wherein the group $R^4OSi(R)_3$ is $CR^5_2(R^6)_aCR^5_2OSi(R)_3$, can be prepared by a process comprising the following steps:

1) reacting a compound represented by formula III or IV

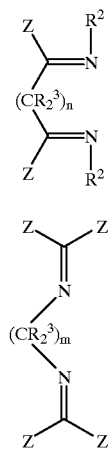

wherein each Z is independently selected from the group consisting of $R^1$ and $CR^5_2H$ provided that at least one Z is $CR^5_2H$; with a Bronsted base preferably selected from the group consisting of: organolithium compound, organosodium compounds, organopotassium compounds, oranomagnesium compounds, sodium hydride, potassium hydride, lithium, sodium, or potassium; preferably lithium alkyl, sodium alkyl, potassium alkyl; more preferably butyllithium;

2) contacting the obtained metallated compound with one equivalent of a compound of general formula $Y(R^6)_n CR^5_2OSi(R)_3$ (as defined above) and wherein Y is a leaving group, preferably halogen, sulfonate groups, more preferably iodine or bromine, and 3) reacting the obtained product with a compound of general formula $L_qMX_2$, wherein M and X have already been defined; L is a labile ligand, i.e. is a weakly coordination group that is removed during the reaction, for example L is a neutral Lewis base such as diethylether, tetrahydrofurane, dimethylaniline, aniline, triphenilphosphine, n-butylamine; 1,2 dimethoxyethane (DME) cyclooctadiene, pyridine, 1,1,2,2-tetramethylendiamine, aromatic or aliphatic nitriles, sulphides, sulphoxides or tioles, triaryl phosphines, arsines or stibines; and q is 1 or 2.

While not wishing to be bound by theory, it is believed that in the above procedure, advantage has been taken of acidity of hydrogen atoms bonded at a carbon in the alpha position to the imino group. Thus, it is believed that following a selection of the base to be used, one acidic proton at the carbon atom at the alpha position of the imino group is removed, resulting in an anionic specie which is believed to be prone to act as a nucleophile in the presence of an electrophile. Thus a new bond can be formed when these two species interact. It is commonly known that such a new bond can be formed through two general pathways: by substitution or by addition. In the first case a leaving group is detached from the electrophilic centre. In the second case, a bond is broken (for instance a double bond becomes a single bond).

In order to have the desired alkoxysilane functional group in the final ligand thus formed, the functional group, or a suitable precursor of it, is preferably already present in the electrophile.

According to this synthetic procedure, choosing an appropriate base is desirable in order to selectively remove a hydrogen atom from the carbon atom in alpha to the imino group and, at the same time, not promoting undesired secondary reactions (for instance addition to the imine double bond). Also a suitable leaving group Y is preferably introduced in the electrophile in order to facilitate the formation of the new bond.

The synthetic method of the present invention has also the advantage of providing the possibility of linking more than just one functional group as long as there are more hydrogen atoms at the carbon atom in an alpha position to any of the two imine groups in the diimine precursor. It is sufficient to adjust the amount of base to be added to the original diimine in order to remove the desired number of hydrogen atoms.

Non limiting examples of compounds represented by formula $YR^5(CR^6{}_7)_n OSi(R)_3$ are:

Cl—CH$_2$—OSiMe$_3$, Cl—CH$_2$—CH$_2$—OSiMe$_3$, Cl—(CH$_2$)$_2$—CH$_2$—OSiMe$_3$, Cl—(CH$_2$)$_3$—CH$_2$—OSiMe$_3$,
Cl—(CH$_2$)$_4$—CH$_2$—OSiMe$_3$, Cl—(CH$_2$)$_5$—CH$_2$—OSiMe$_3$, Cl—CH$_3$—(CH$_2$)$_6$—CH$_2$—OSiMe$_3$,
Cl—(CH$_2$)$_7$—CH$_2$—OSiMe$_3$, Cl—C$_6$H$_4$—CH$_3$—OSiMe$_3$, Cl—(CH$_2$)$_8$—CH$_2$—OSiMe$_3$,
Cl—(CH$_2$)$_9$—CH$_2$—OSiMe$_3$, Cl—(CH$_2$)$_{10}$—CH$_2$—OSiMe$_3$, Cl—CH$_2$—CMe$_2$—CH$_2$—OSiMe$_3$,
Cl—CH$_2$—CMe$_2$—CH$_2$—CH$_2$—OSiMe$_3$, Cl—CH$_2$—CMe$_2$—CMe$_2$—CH$_2$—OSiMe$_3$,
Cl—CH$_2$—C$_6$H$_4$—O—CH$_2$—OSiMe$_3$, Cl—CMe$_2$—CH$_2$—OSiMe$_3$, Cl—CH$_2$—CEtMe—CH$_2$—OSiMe$_3$,
Cl—CH$_2$—CEt$_2$—CH$_2$—CH$_2$—OSiMe$_3$, Cl—CH$_2$—CMe$_2$—CEt$_2$—CH$_2$—OSiMe$_3$,
Cl—CH$_2$—C$_6$H$_4$—O—CH$_2$—OSiMe$_3$, Cl—CEt$_2$—CH$_2$—OSiMe$_3$,
Br—CH$_2$—OSiMe$_3$, Br—CH$_2$—CH$_2$—OSiMe$_3$, Br—(CH$_2$)$_2$—CH$_2$—OSiMe$_3$, Br—(CH$_2$)$_3$—CH$_2$—OSiMe$_3$,
Br—(CH$_2$)$_4$—CH$_2$—OSiMe$_3$, Br—(CH$_2$)$_5$—CH$_2$—OSiMe$_3$, Br—(CH$_2$)$_6$—CH$_2$—OSiMe$_3$,
Br—(CH$_2$)$_7$—CH$_2$—OSiMe$_3$, Br—CH$_2$—C$_6$H$_4$—CH$_2$—OSiMe$_3$, Br—(CH$_2$)$_8$—CH$_2$—OSiMe$_3$,
Br—(CH$_2$)$_9$—CH$_2$—OSiMe$_3$, Br—(CH$_2$)$_{10}$—CH$_2$—OSiMe$_3$, Br—CH$_2$—CMe$_2$—CH$_2$—OSiMe$_3$,
Br—(CH$_2$—CMe$_2$—CH$_2$—CH$_2$—OSiMe$_3$, Br—CH$_2$—CMe$_2$—CM$_2$—CH$_2$—OSiMe$_3$,
Br—CH$_2$—C$_6$H$_4$—O—CH$_2$—OSiMe$_3$, Br—CMe$_2$—CH$_2$—OSiMe$_3$, Br—CH$_2$—CEtMe—CH$_2$—OSiMe$_3$,
Br—CH$_2$—CEt$_2$—CH$_2$—CH$_2$—OSiMe$_3$, Br—CH$_2$—CMe$_2$—CEt$_2$—CH$_2$—OSiMe$_3$,
Br—CH$_2$—C$_6$H$_4$—O—CH$_2$—OSiMe$_3$, Br—CEt$_2$—CH$_2$—OSiMe$_3$,
I—CH$_2$—OSiMe$_3$, I—CH$_2$—CH$_2$—OSiMe$_3$, I—(CH$_2$)$_2$—CH$_2$—OSiMe$_3$, I—(CH$_2$)$_3$—CH$_2$—OSiMe$_3$,
I—(CH$_2$)$_4$—CH$_2$—OSiMe$_3$, I—(CH$_2$)$_5$—CH$_2$—OSiMe$_3$, I—(CH$_2$)$_6$—CH$_2$—OSiMe$_3$,
I—(CH$_2$)$_7$—CH$_2$—OSiMe$_3$, I—CH$_2$—C$_6$H$_4$—CH$_2$—OSiMe$_3$, I—(CH$_2$)$_8$—CH$_2$—OSiMe$_3$,
I—(CH$_2$)$_9$—CH$_2$—OSiMe$_3$, I—(CH$_2$)$_{10}$—CH$_2$—OSiMe$_3$, I—CH$_2$—CMe$_2$—CH$_2$—OSiMe$_3$,
I—CH$_2$—CMe$_2$—CH$_2$—CH$_2$—OSiMe$_3$, I—CH$_2$—CMe$_2$—CMe$_2$—CH$_2$—OSiMe$_2$, I—CH$_2$—C$_6$H$_4$—O—CH$_2$—OSiMe$_3$,
I—CMe$_2$—CH$_2$—OSiMe$_3$, I—CH$_2$—CEtMe—CH$_2$—OSiMe$_3$, I—CH$_2$—CEt$_2$—CH$_2$—CH$_2$—OSiMe$_3$,
I—CH$_2$—CMe$_2$—CEt$_2$—CH$_2$—OSiMe$_3$, I—CH$_2$—C$_6$H$_4$—O—CH$_2$—OSiMe$_3$, I—CEt$_2$—CH$_2$—OSiMe$_3$,
I—CH$_2$—OSiEt$_3$, I—CH$_2$—CH$_2$—OSiEt$_3$, I—(CH$_2$)$_2$—CH$_2$—OSiEt$_3$, I—(CH$_2$)$_3$—CH$_2$—OSiEt$_3$,
I—(CH$_2$)$_4$—CH$_2$—OSiEt$_3$, I—(CH$_2$)$_5$—CH$_2$—OSiEt$_3$, I—(CH$_2$)$_6$—CH$_2$—OSiEt$_3$,
Br—(CH$_2$)$_7$—CH$_2$—OSiPr$_3$, Br—CH$_2$—C$_6$H$_4$—CH$_2$—OSiPr$_3$, Br—(CH$_2$)$_8$—CH$_2$—OSiPr$_3$,
Br—(CH$_2$)$_9$—CH$_2$—OSiPr$_3$, Br—(CH$_2$)$_{10}$—CH$_2$—OSiPr$_3$, Br—CH$_2$—CMe$_2$—CH$_2$—OSiPr$_3$,
Cl—CH$_2$—CMe$_2$—CH$_2$—CH$_2$—OSiPh$_3$, Cl—CH$_2$—CMe$_2$—CMe$_2$—CH$_2$—OSiPh$_3$,
Cl—CH$_2$—C$_6$H$_4$—O—CH$_2$—OSiPh$_3$, Cl—CMe$_2$—CH$_2$—OSiPh$_3$, Cl—CH$_2$—CEtMe—CH$_2$—OStPh$_3$,
Cl—CH$_2$—CEt$_2$—CH$_2$—CH$_2$—OSiPh$_3$, Br—CH$_2$—CMe$_2$—CEt$_2$—CH$_2$—OSiMeEt$_2$,
Br—CH$_2$—C$_6$H$_4$—O—CH$_2$—OSiPhMe$_2$, Br—CEt$_2$—CH$_2$—OSiEtPr2.

More preferred diimino compounds of formula I are:

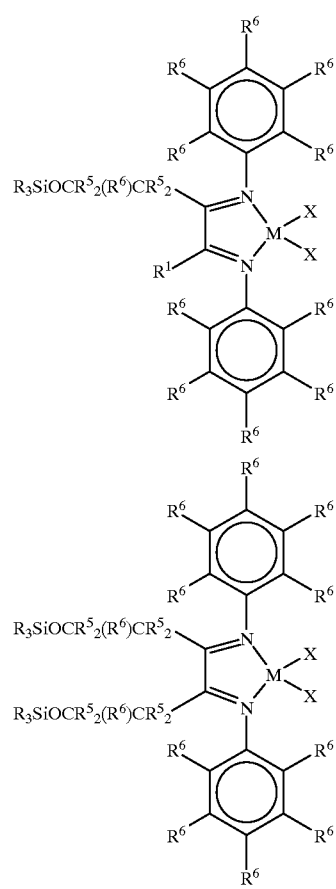

Non limitative examples of compounds according to formula 1 are:
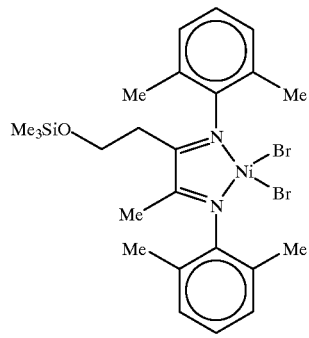
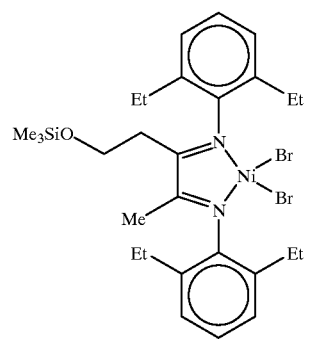
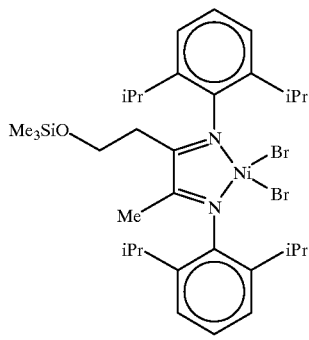
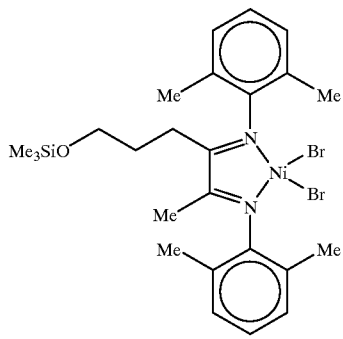
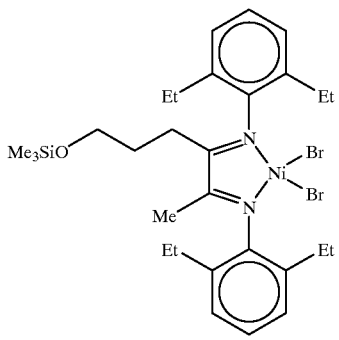
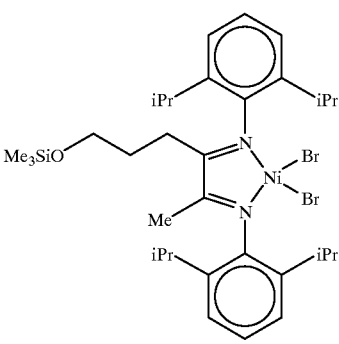
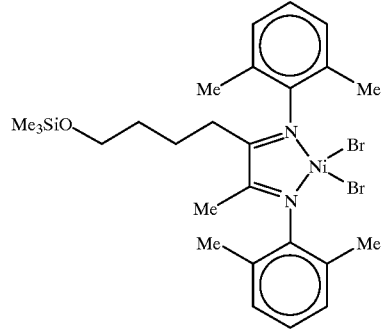
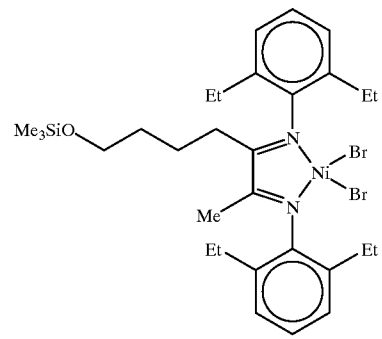

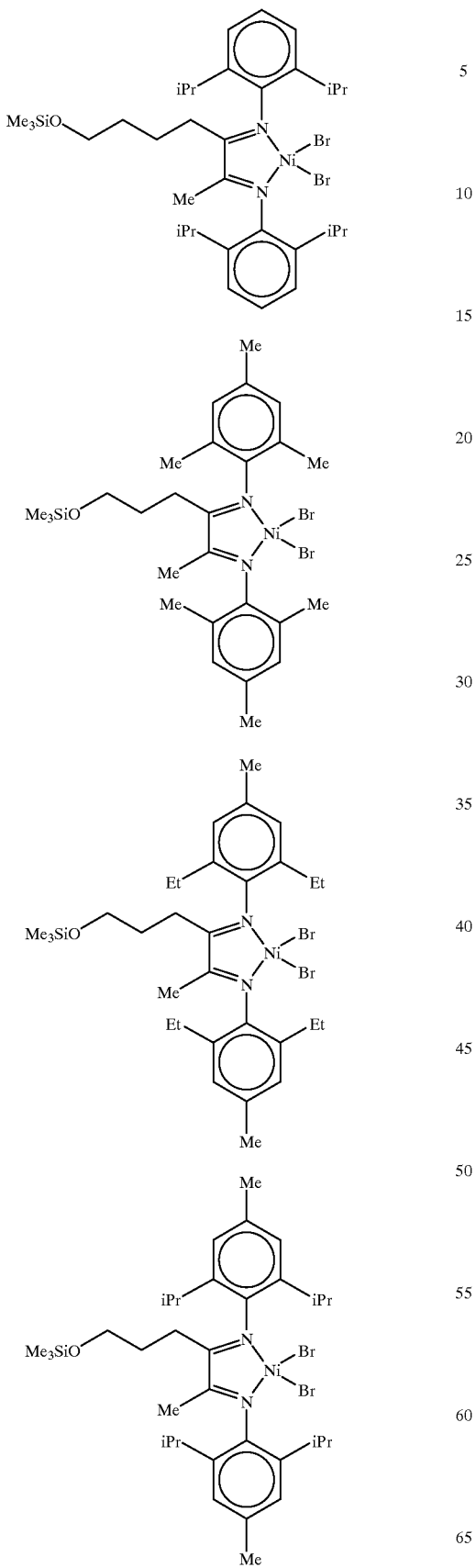
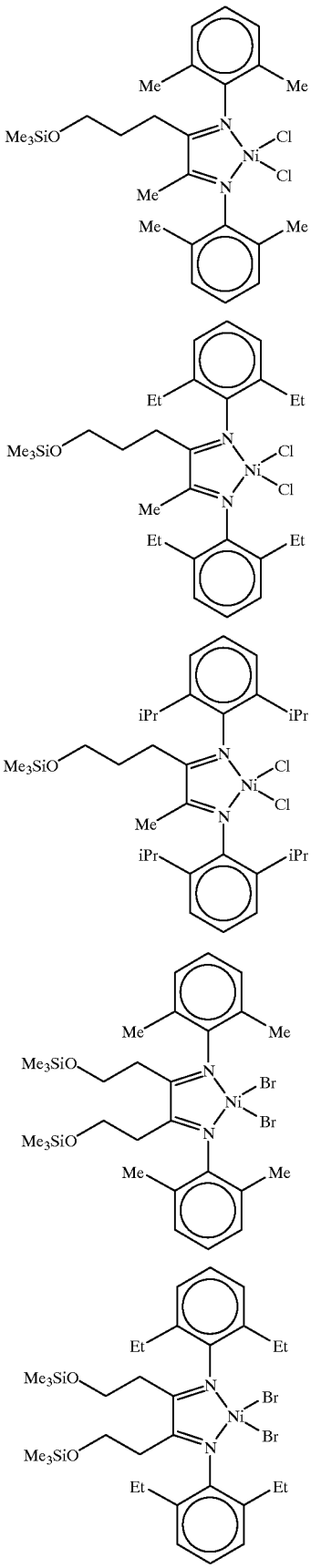

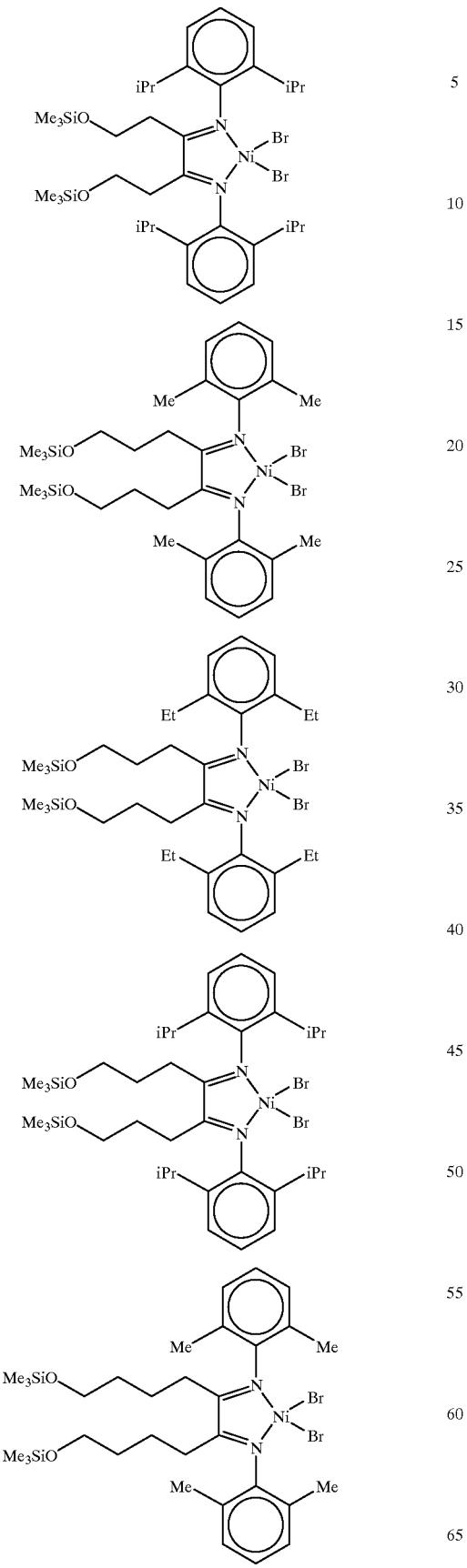
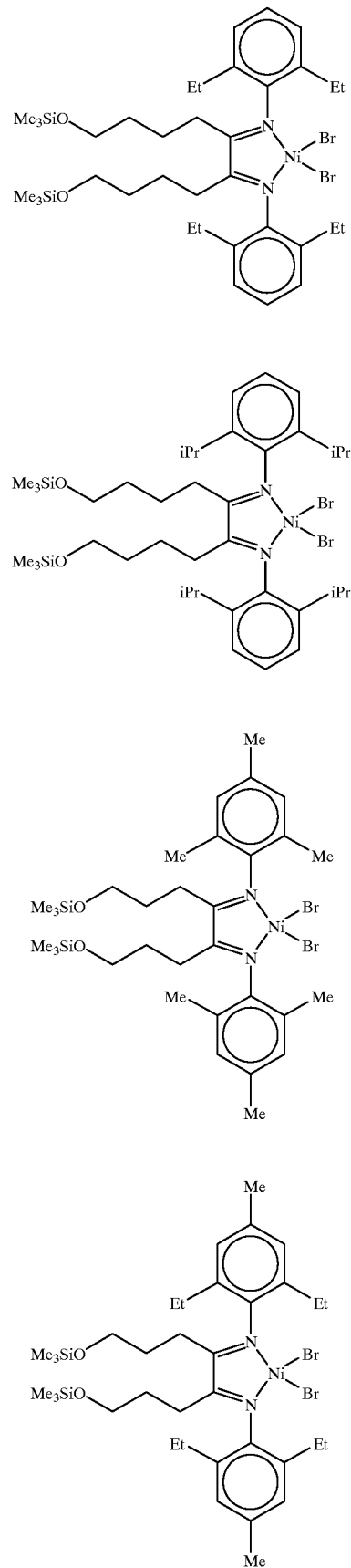

-continued
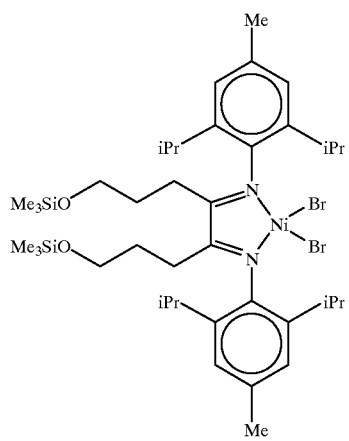
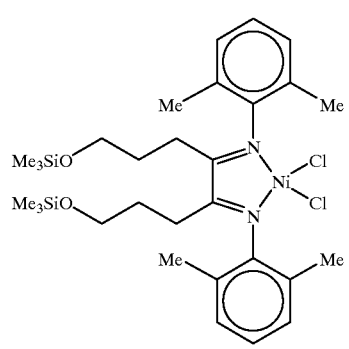
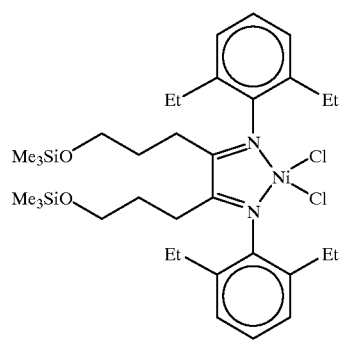
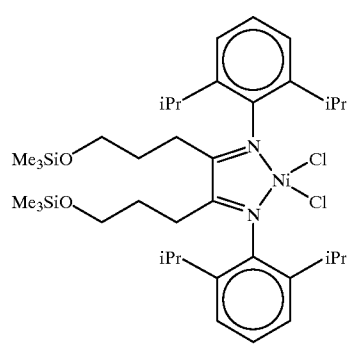
-continued
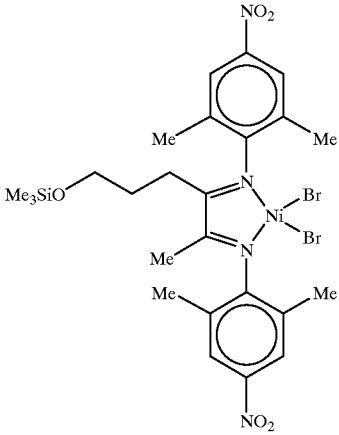

-continued
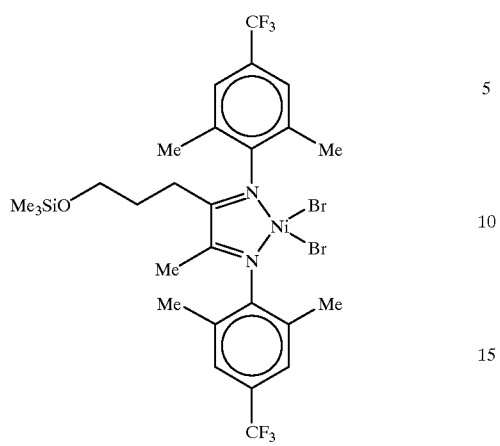
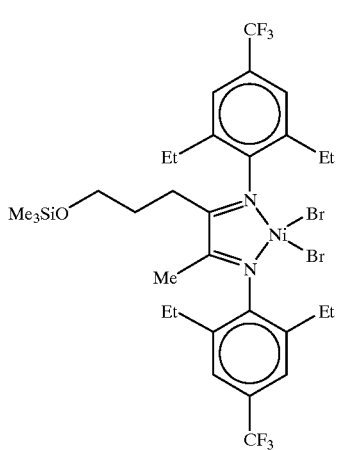
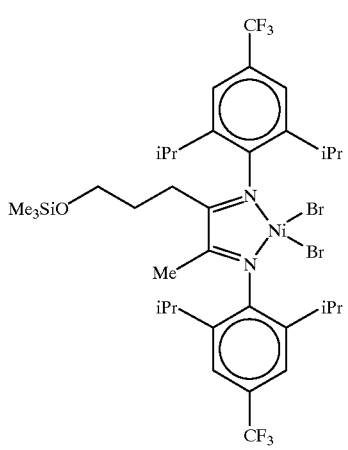
-continued
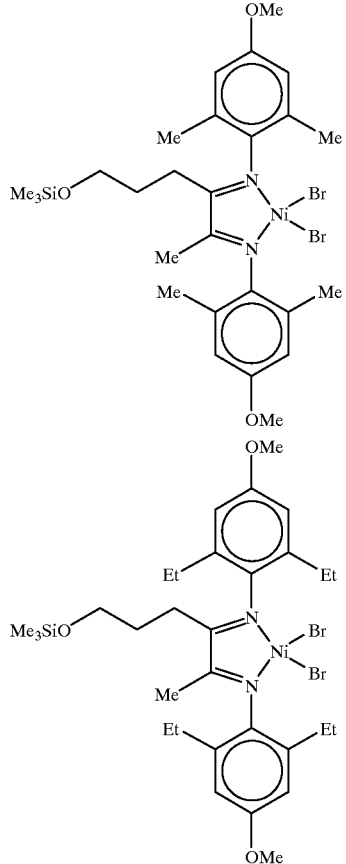
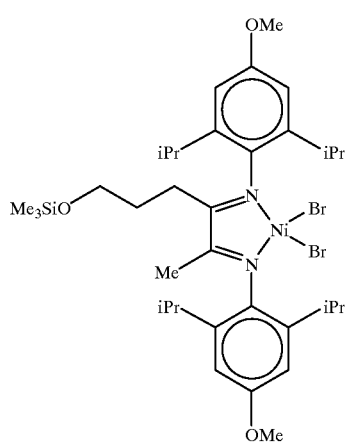
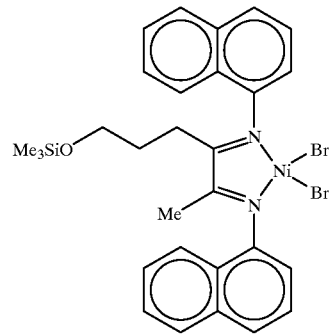

-continued
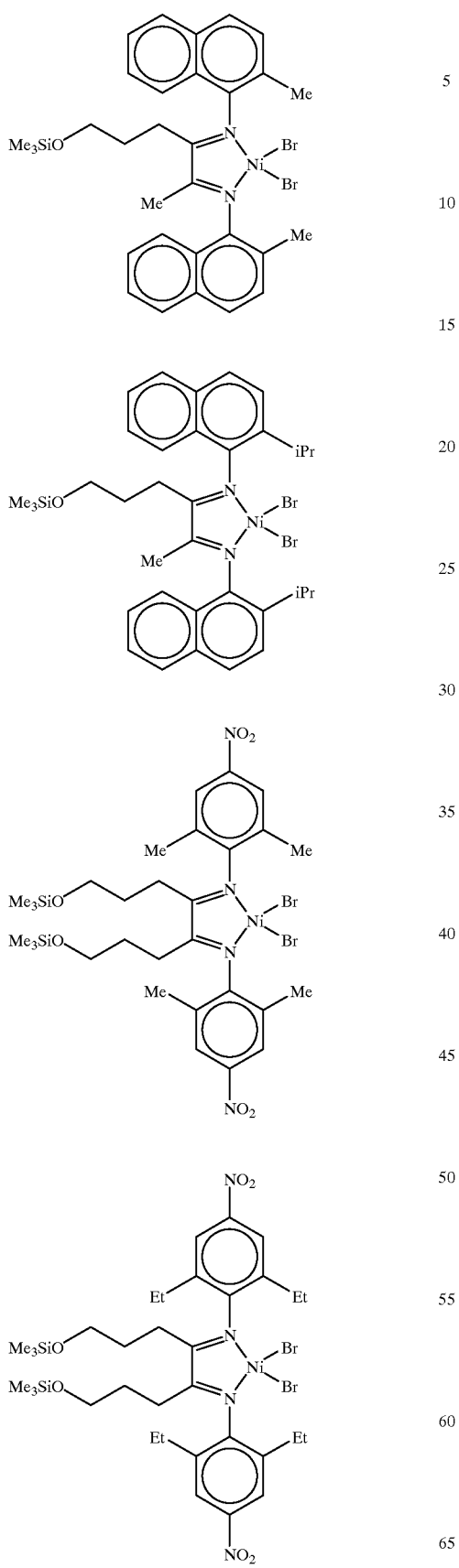
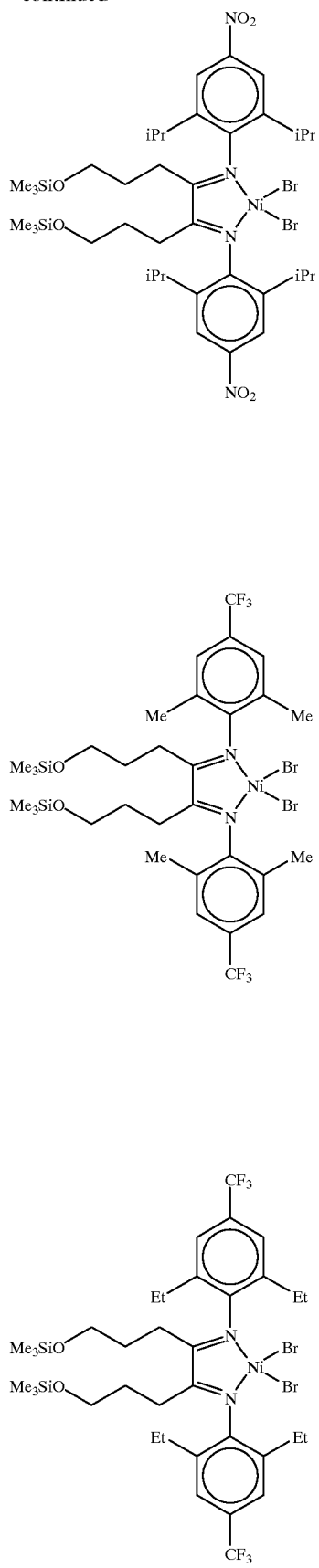

-continued
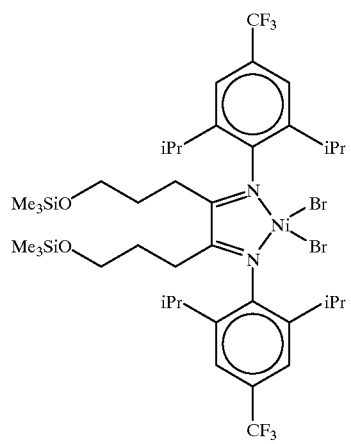
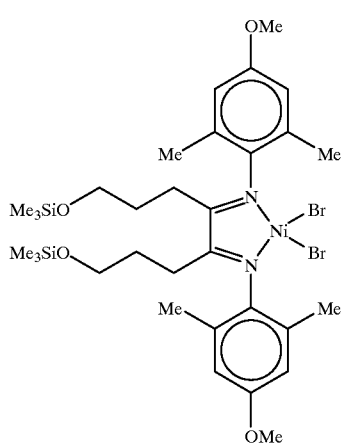
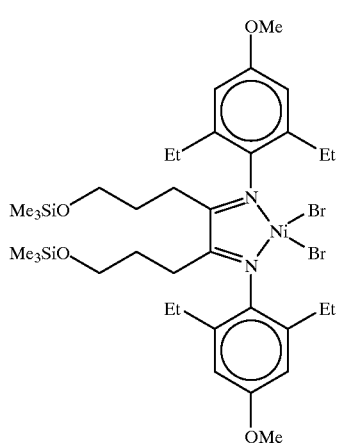
-continued
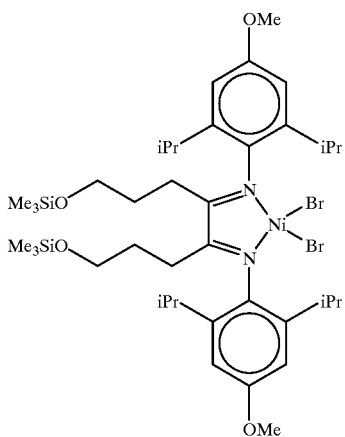
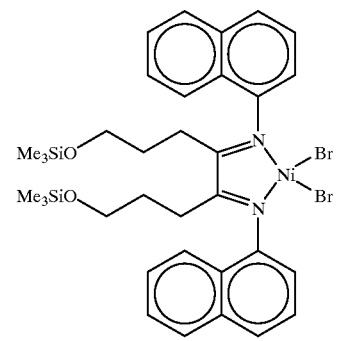
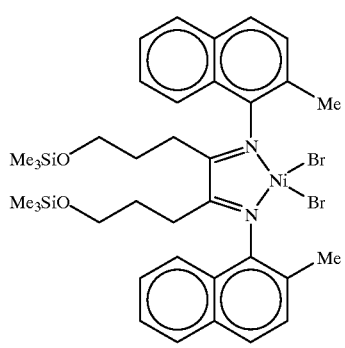
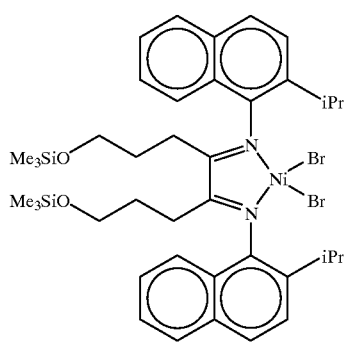

-continued
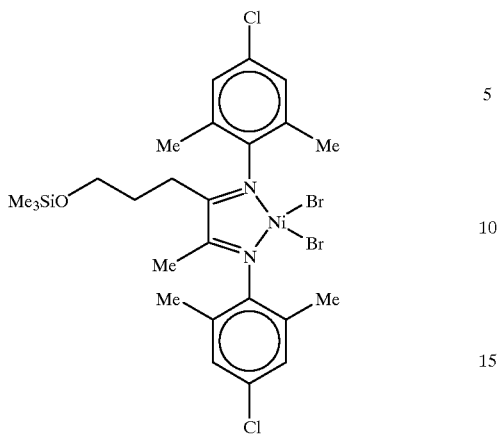
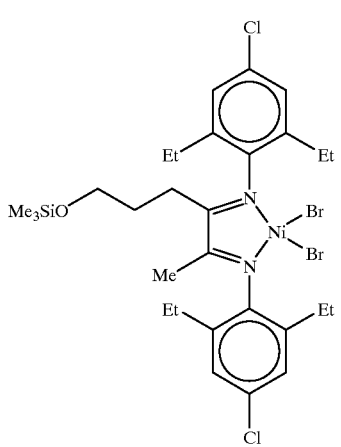
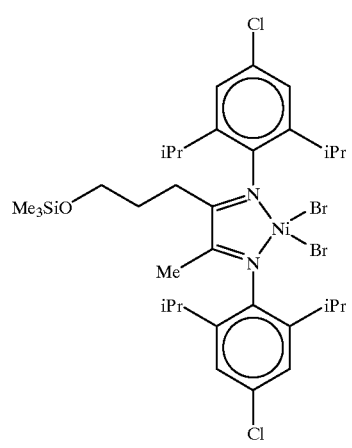
-continued
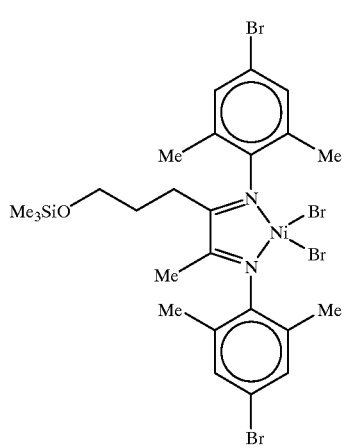
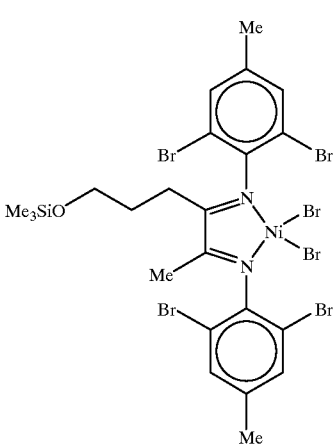
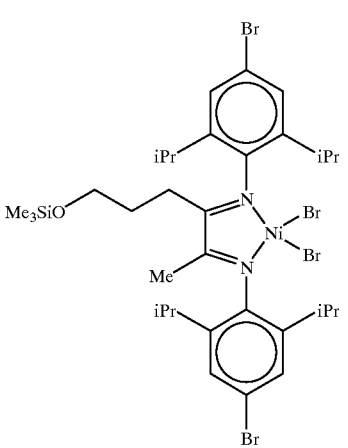
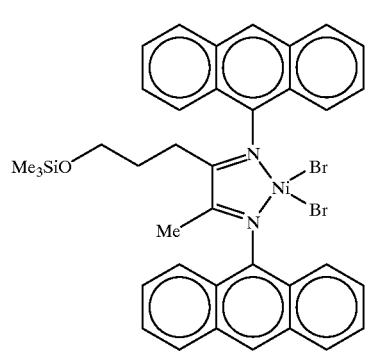

-continued
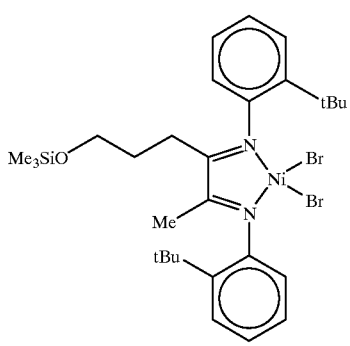
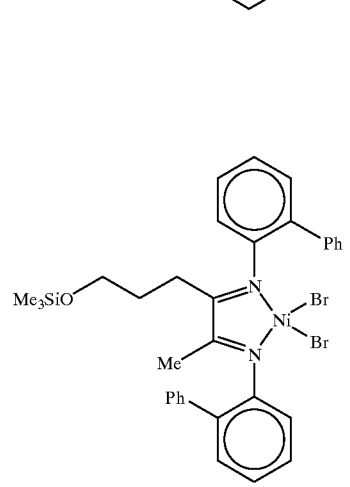
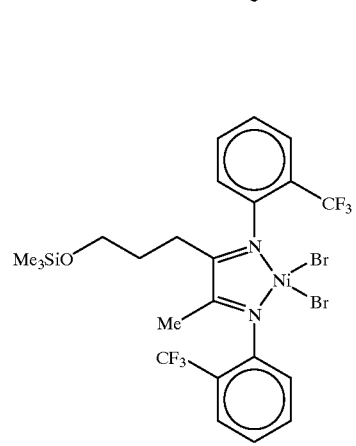
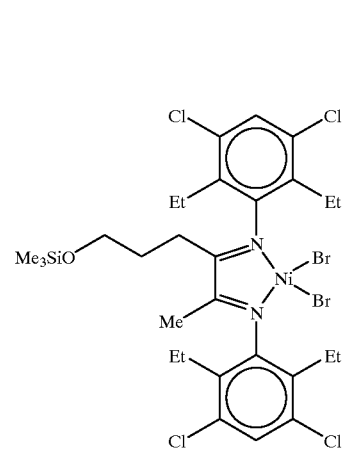
-continued
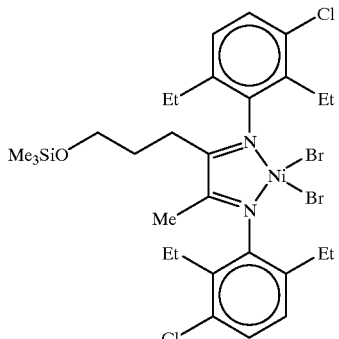
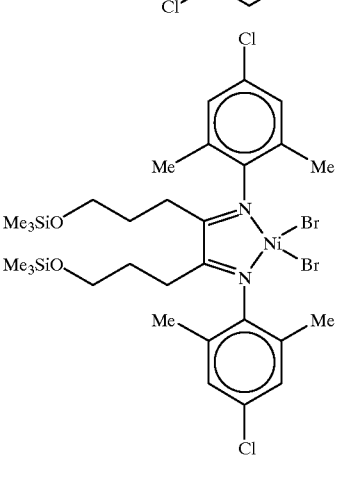
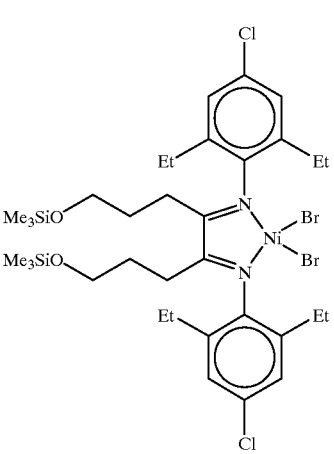
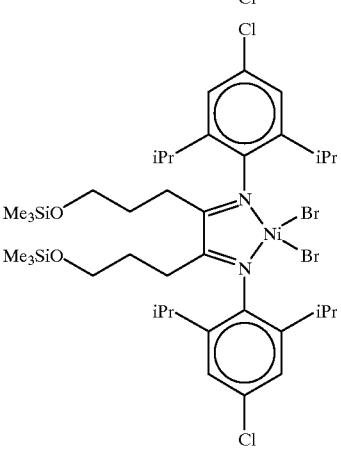

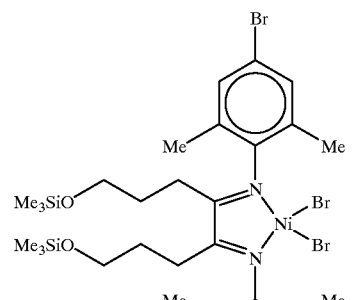
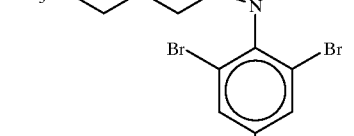
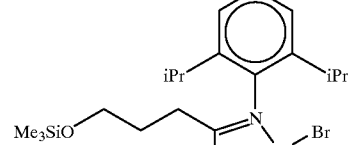
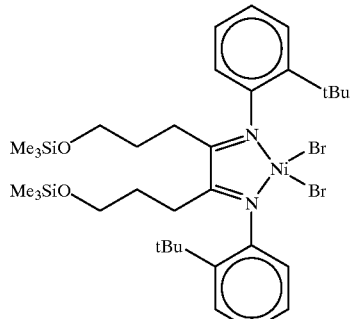
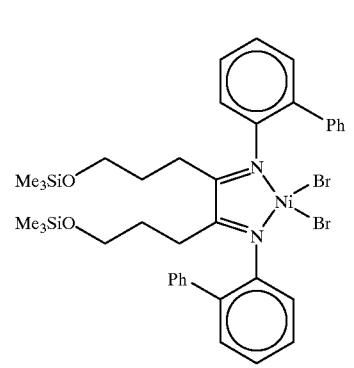
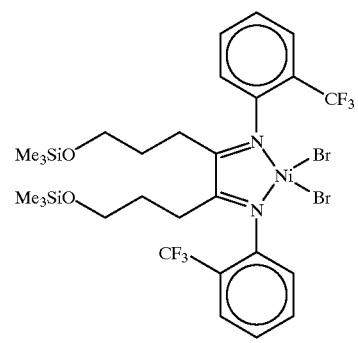
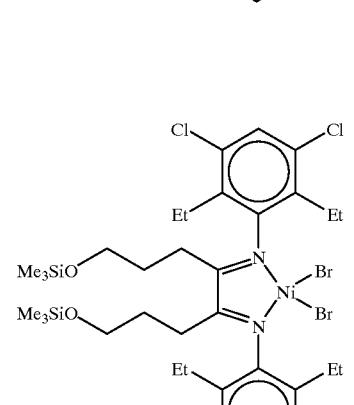

-continued
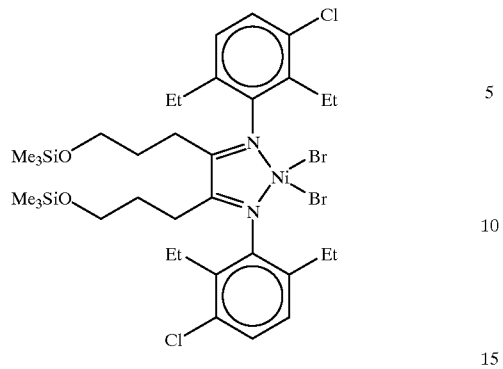
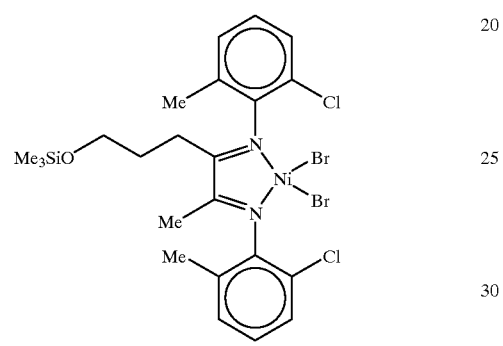
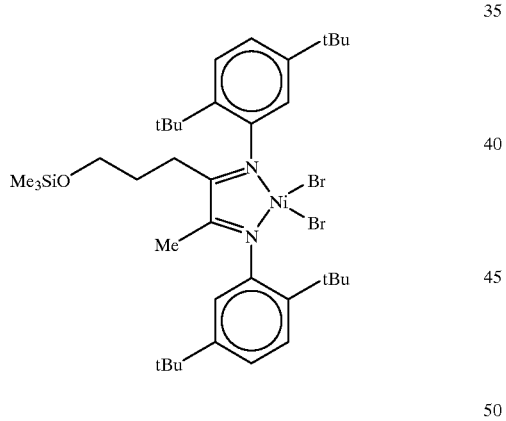
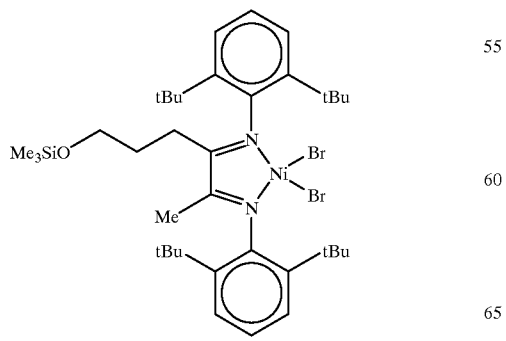
-continued
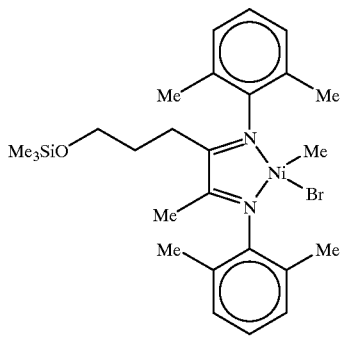
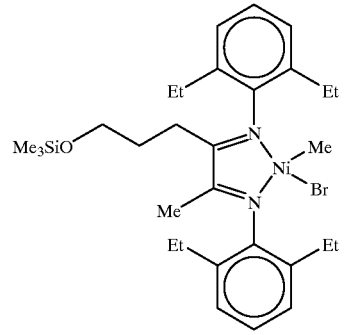
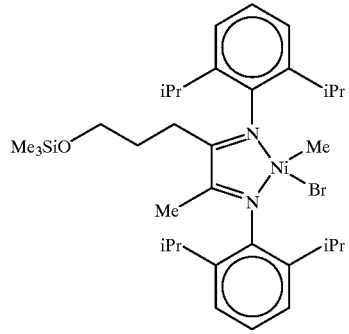
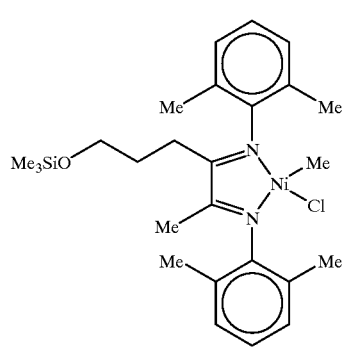

-continued
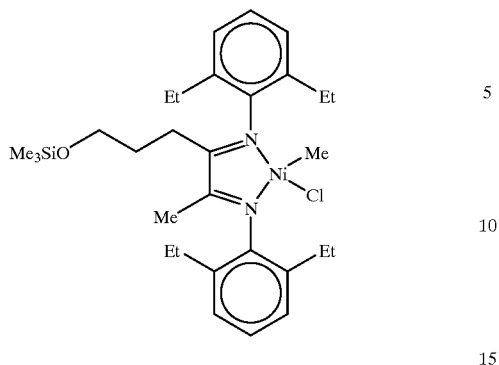
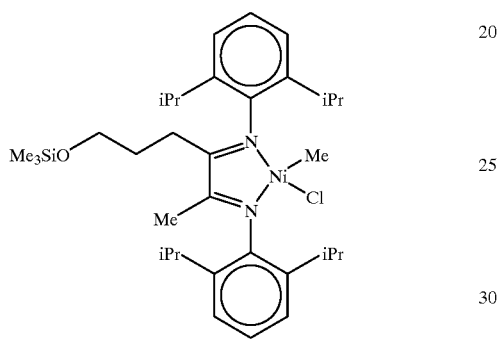
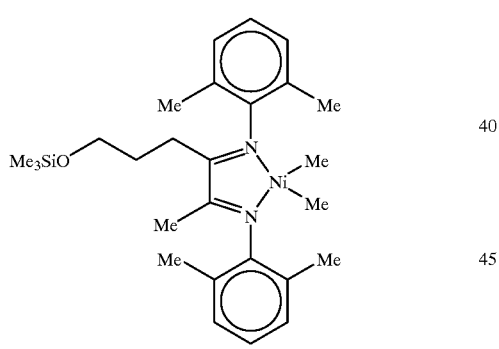
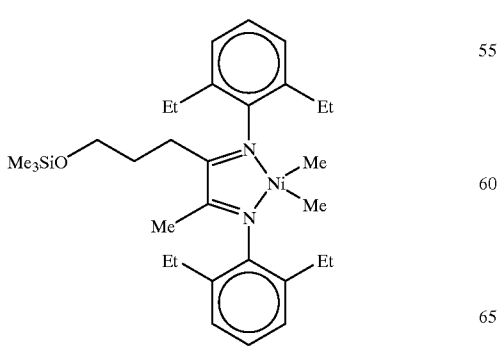
-continued
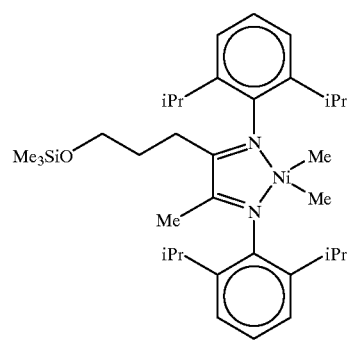
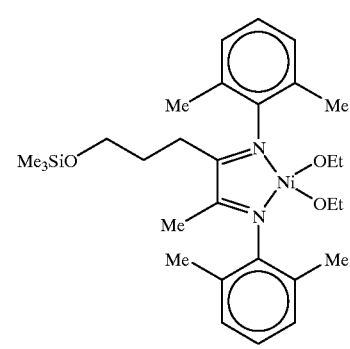
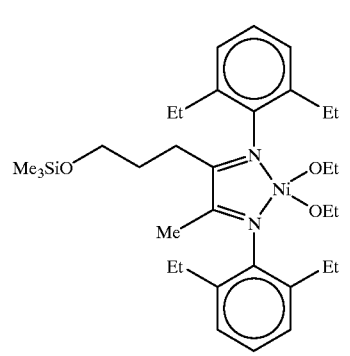
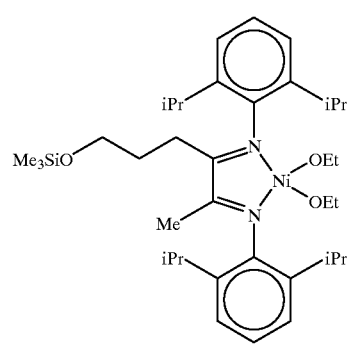

-continued
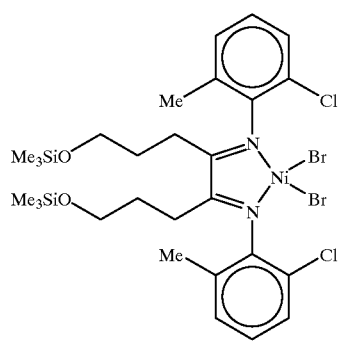
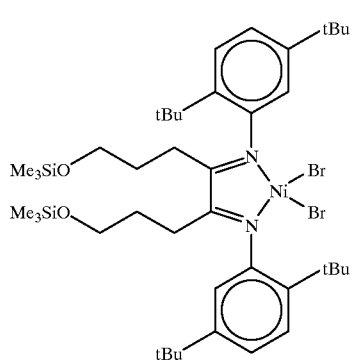
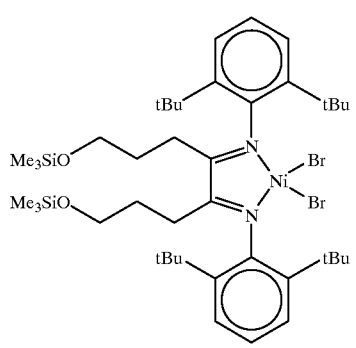
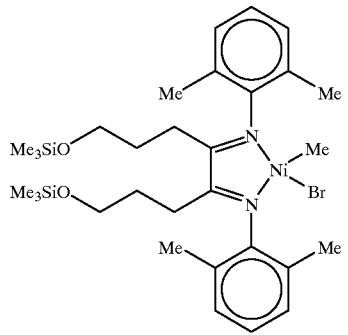
-continued
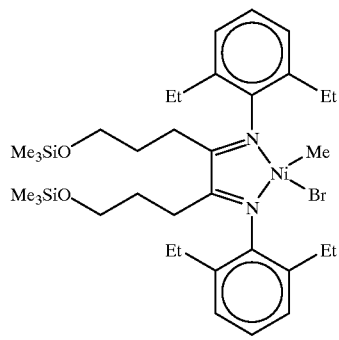
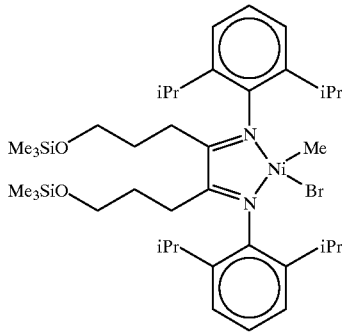
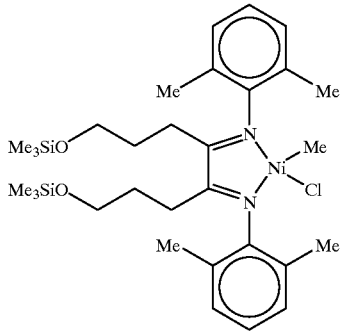
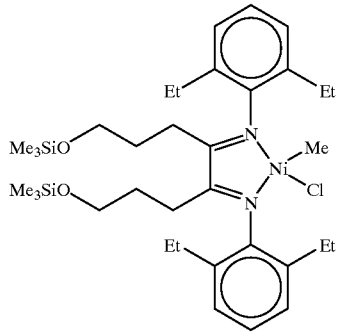
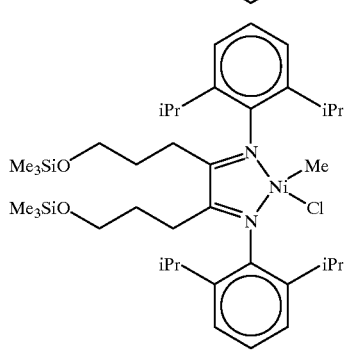

-continued
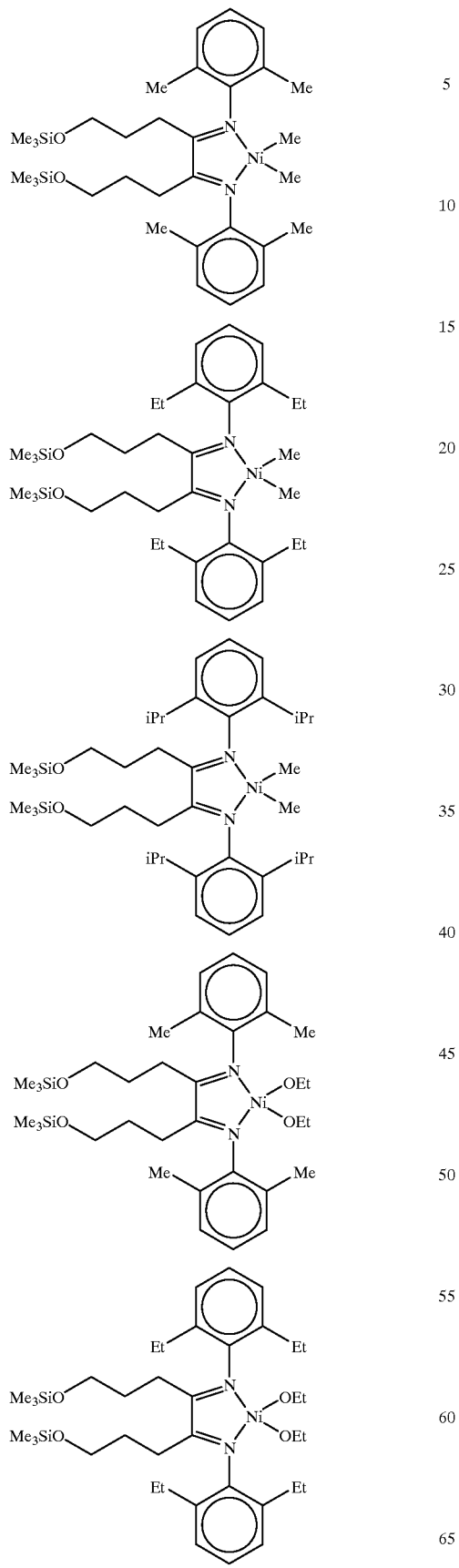
-continued
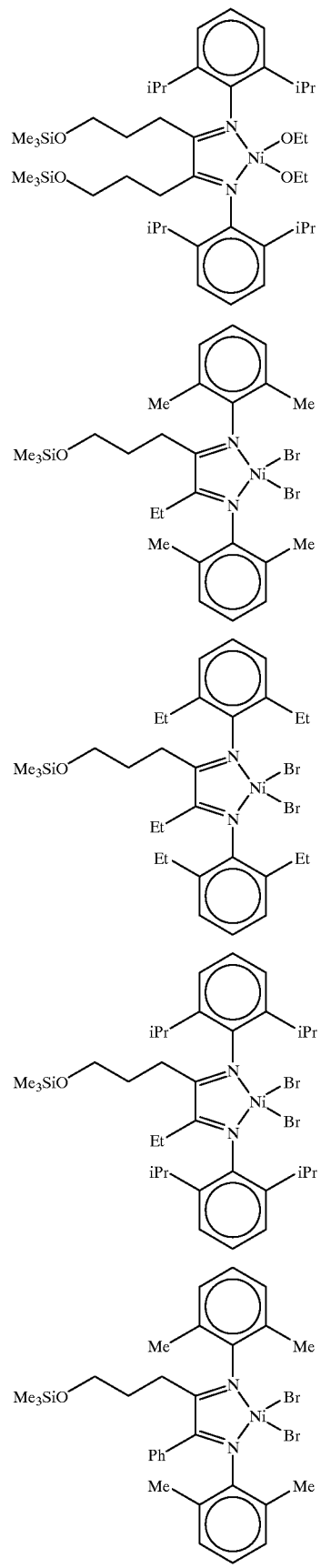

-continued
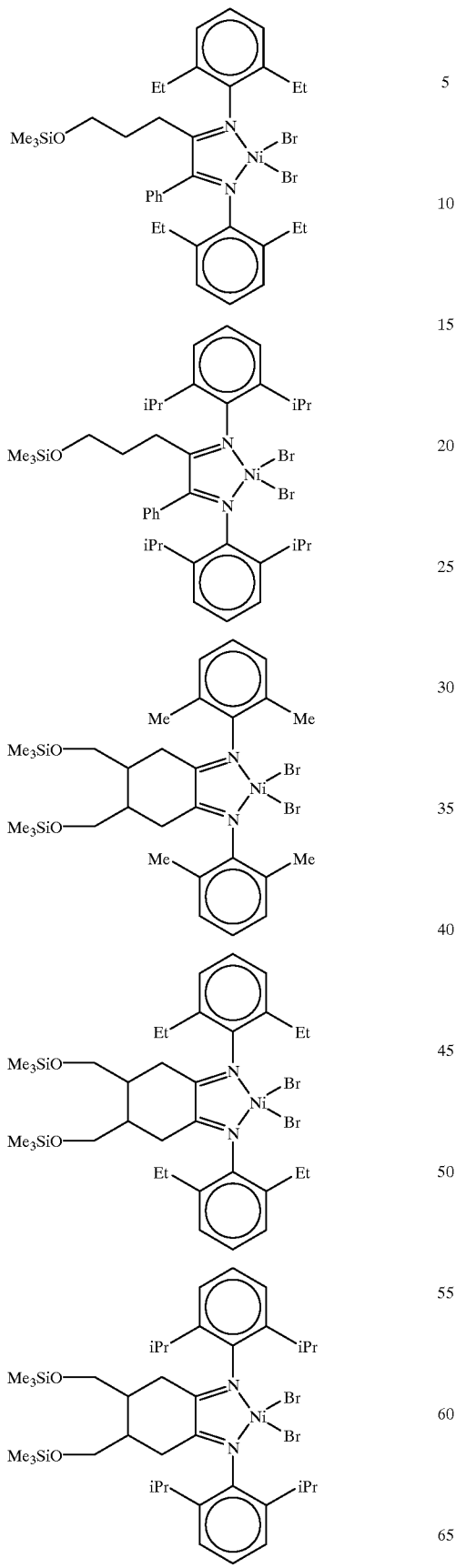
-continued
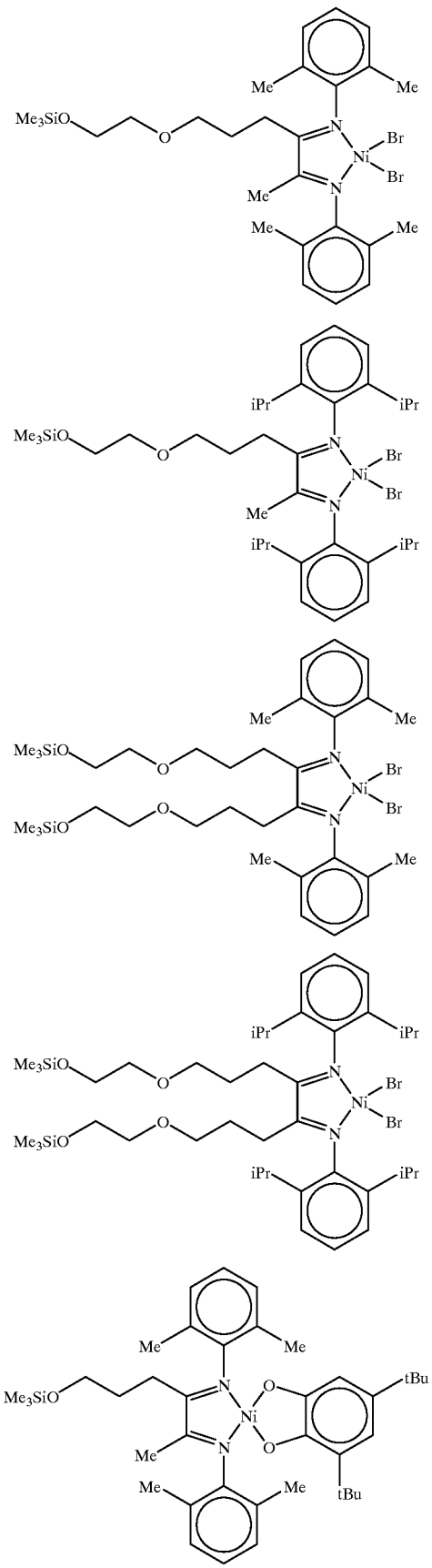

-continued
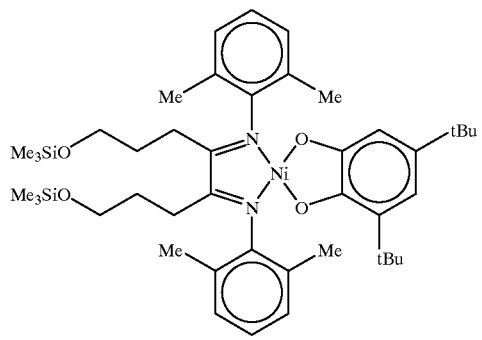
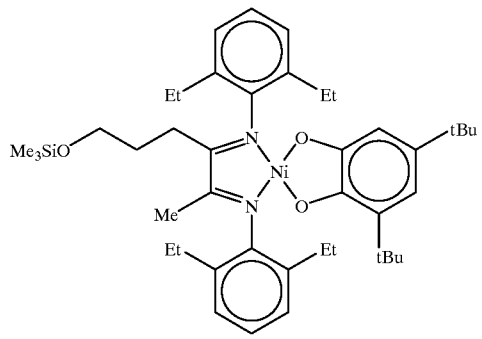
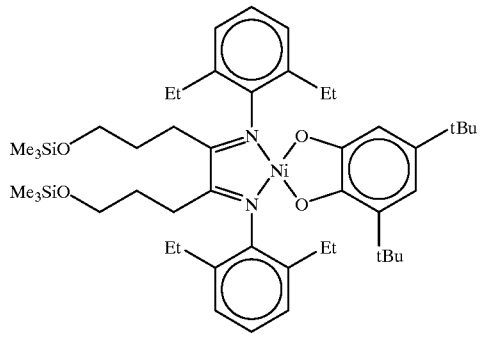
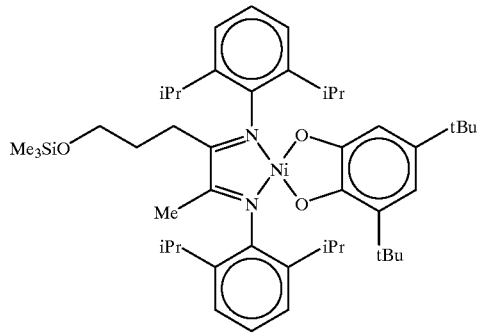
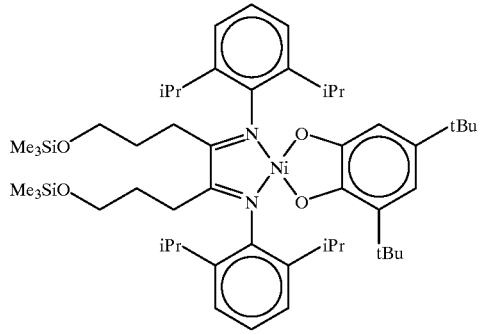
-continued
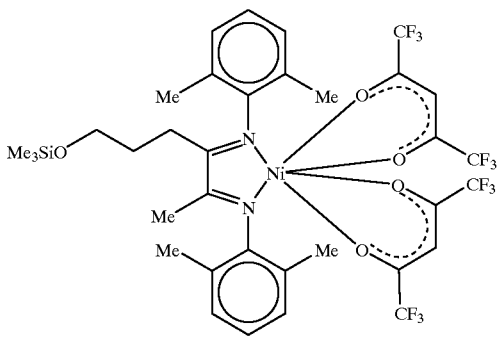
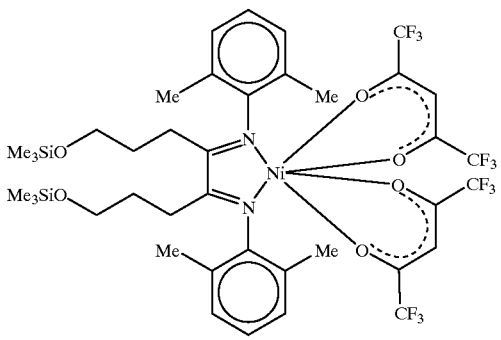
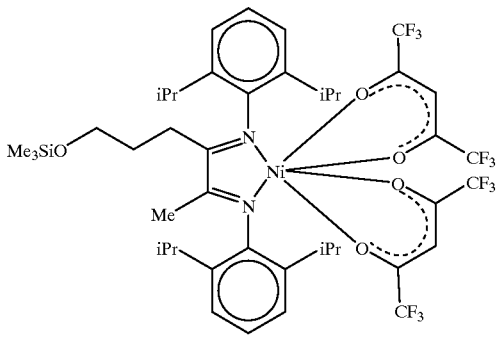
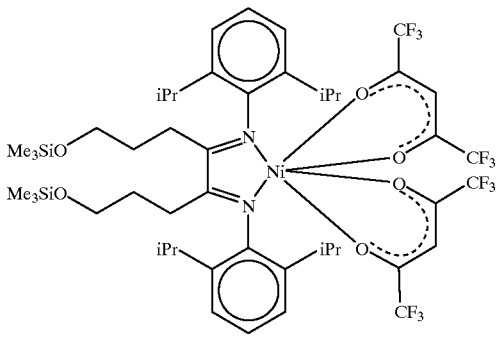
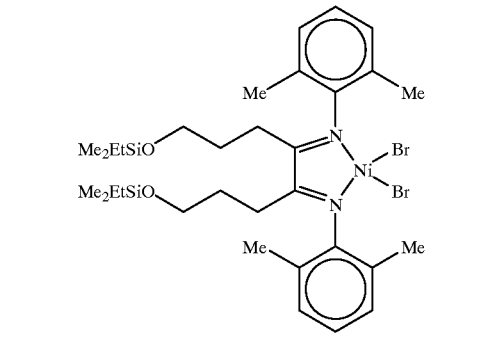

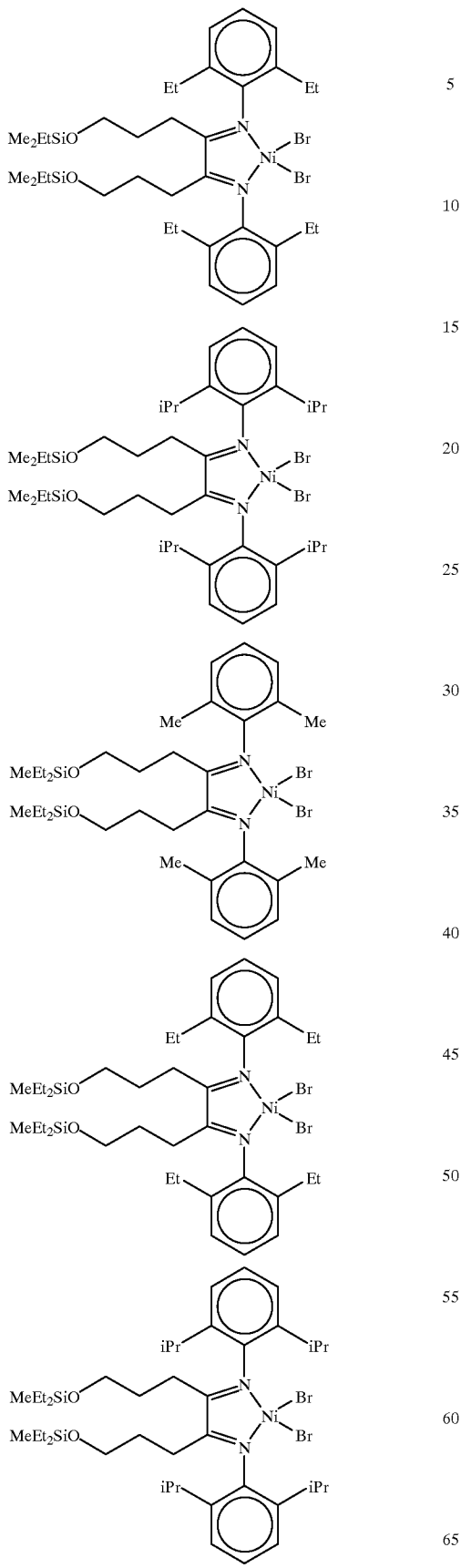
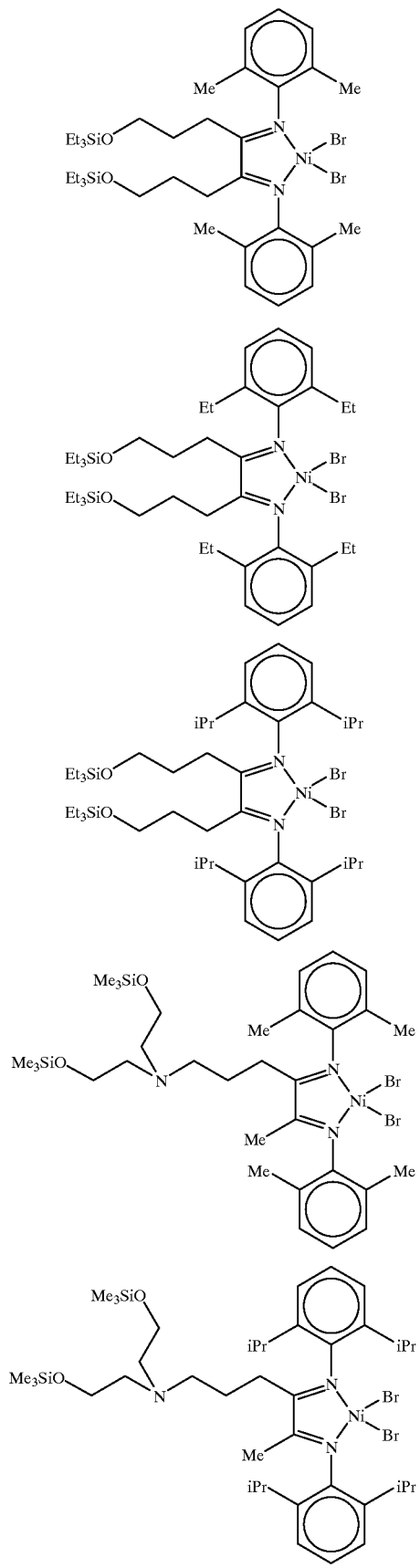

The compounds of the present invention can be used as catalyst components for polymerizing olefins, preferably alpha-olefins. This catalyst component is especially useful for the production of branched polyethylene without requiring co-monomer. The catalyst component of the present invention is preferably used in combination with a cocatalyst. Illustrative but non-limiting examples of co-catalysts are: aluminoxanes (methylaluminoxane (MAO), modified methylaluminoxane (MMAO), isobutylaluminoxane (IBAO), etc.), combinations of alkylaluminiums (such as trimethylaluminium, trimethylaluminium, tributylaluminium, etc.) and boron containing Lewis acids (such as trifluoroborate, trispentafluorophenylborane, tris[3, 5-bis(trifluoromethyl)phenyl]borane, etc.), hydrogen Lewis acids (dimethylanilinium tetrakis(pentafluorophenyl)boron, $HBF_4$, etc.), silver Lewis acids (such as $AgBF_4$, $AgPF_6$, $AgSbF_6$, silver tetrakis[3,5-bis(trifluoromethyl)phenyl] borate etc.) or others (such as sodium tetrakis[3,5-bis (trifluoromethyl)phenyl]borate, etc.).

The catalyst component of the present invention is especially useful for being supported on a porous inorganic solid. As supporting material, any type of inorganic oxides can be used, such as: silica, alumina, silica-alumina, aluminum phosphates and mixtures thereof, obtaining supported catalysts with contents in transition metals between 0.01 and 10% by weight, preferably between 0.1 and 4%. Particularly preferred supports are silica calcined at a temperature between 600° C. and 800° C., and silica previously treated with alumoxane.

A process for preparing supported catalysts according to this invention comprises the following steps:
 a) contacting, preferably under anhydrous conditions and inert atmosphere, a solution of at least one diimino-complex of the present invention, with the support material at a temperature between −20° C. and 90° C.; and
 b) filtering and washing with a solvent, selected from aliphatic or aromatic hydrocarbon, or a mixture thereof.

Another process that can be used comprises the following steps:
 a) contacting, preferably under anhydrous conditions and inert atmosphere, a solution of at least one diimino-complex of the present invention, with the support material at a temperature between −20° C. and 90° C.;
 b) eliminating the solvent preferably through evaporation;
 c) warming the solid residue up to temperature between 25 and 150° C.

The solid catalyst obtained by this process can be further subjected to washing and subsequent filtration.

The amount of the diimino-complex which can be anchored onto the support with the above methods directly relates to the concentration of the reactive groups present in the support. For this reason silica, for example, should preferably have been calcinated at a temperature between 600° C. and 800° C., preferably in a dry atmosphere.

An advantageous aspect of this invention is that the support method, presumably as a consequence of the reaction of group —$OSi(R)_3$ with reactive groups of the support surface, appears to prevent the desorption of the supported diimino-complexes. This type of interaction represents a significant difference between the organo-complexes heterogenization mechanism and other conventional methods, where the diimino-complex generally remains physisorbed on the support surface.

The procedure employed for the formation of the catalyst results in little or no by-products that could hamper the polymerisation process. Thus, no extra reactants other than the functionalized complex and the silica are needed. Thus, in a preferred embodiment, scavengers and other agents to neutralize the by-products are not used.

The choice of diimino ligand and metal can result in a highly active catalyst for the polymerisation of olefins. The properties of the polyolefins so obtained can be finely tuned by a selection of the structural properties of the diimine ligand attached to the silica, the nature of the metal centre employed and the polymerisation conditions used (e.g. temperature, pressure, concentration of reactants, etc.).

A solid catalyst system can be obtained by adding to the solid catalyst component a cocatalyst, for example alumoxane, boron compounds or mixtures thereof, at any step of the processes described above. For example, catalyst systems can be obtained by reacting silica with the bidentate diimino-complex and then adding alumoxane or treating silica with alumoxane and then reacting the obtained carrier with the bidentate diimino-complex.

For the polymerization in solution, the cocatalyst can be mixed with a solution of a diimino-complex of formula I or II and a supplementary quantity of cocatalyst can be added to the solution; or the catalyst can directly be added to the polymerization medium, which contains the cocatalyst.

For the polymerization in suspension, the cocatalyst can previously be mixed with the supported solid catalyst or it can be added to the polymerization medium before the supported catalyst, or both operations can be sequentially realized.

The most useful polymerization procedure can change according to the chosen type of polymerization process (solution, suspension, slurry or gas phase).

In general, the process comprises contacting the monomer, or, in certain cases, the monomer and the comonomer, with a catalytic composition according to the present invention, that includes at least one diimino-complex of formula I or II.

The alpha-olefins that can be used as comonomers to obtain ethylene copolymers can be one or more $C_3$–$C_{12}$ linear or branched alpha olefin, such as propylene, butene, hexene, octene and 4-methyl-1-pentene and can be used in proportions from 0.1 to 70% by weight of the total of the monomers. In the case of polymerization of ethylene the density of polymers can be as low as 0.86 g/cm$^3$.

In the particular case of gas-phase suspension process or controlled particle morphology process, the used temperature will be preferably between 30° and 100° C., while for the solution process the usual temperature will be between 120° and 250° C.

The pressure will change according to the polymerization technique and may range from atmospheric pressure to 350 MPa.

EXAMPLES

Metal Complex Synthesis

All operations were carried out under nitrogen or argon atmosphere following conventional Schlenk techniques. THF and diethyl ether were dried by distillation from sodium and benzophenone; $CH_2Cl_2$ was dried by distillation from calcium hydride; petroleum ether and toluene was dried by distillation from sodium. All solvents were degassed before use. The petroleum ether had a boiling point of 40–60° C.

Example 1

Preparation of 1-trimethylsilyloxy-2-iodoethane, $ICH_2CH_2OSiMe_3$.

To a solution of 2-iodoethanol (3.9 ml, 50 mmol) and triethylamine (7.25, 52 mmol) in THF (40 ml) stirred at 0°

C., was added trimethylsilyl chloride (6.36 ml, 50 mmol). The stirring was continued for 0.5 h at the same temperature and for 6 h at room temperature. Evaporation of the solvent and distillation under vacuum affords 9.71 g of the title compound as a colourless liquid (80% yield).

$^1$H NMR (CDCl$_3$, 400 MHz) δ 3.80 (t, 2H, CH$_2$—OSiMe$_3$), 3.19 (t, 2H, CH$_2$—I), 0.14 (s, 9H, OSiMe$_3$); $^{13}$C{$^1$H} NMR (CDCl$_3$, 100 MHz) δ 63.7 (CH$_2$—OSiMe$_3$), 6.6 (CH$_2$—I), −0.3 (OSiMe$_3$).

Example 2

Monofunctionalization of Diimine Ligands (General Procedure)

A solution of t-BuLi in pentane (1.7M, 2.4 ml, 4.1 mmol) was added dropwise over a stirred solution of the corresponding N,N'-bis(2,6-dialkylphenyl)-1,4-diaza-2,3-dimethyl-1,3-butadiene (4 mmol) in 20 ml of THF at −80° C. After ca. 1 min, the yellow coloured solution turns to red. The reaction mixture was then stirred for 1 h and ICH$_2$CH$_2$OSiMe$_3$ (1 g, 4.1 mmol) was added. The stirring was continued for 0.5 h, and then for 6 h at room temperature. The solvent was removed under vacuum and the residue extracted with 20 ml of petroleum ether. Filtration and evaporation of the solvent affords the product as yellowish-green oil in ca 90% yields.

Example 2.1

Synthesis of [N,N'-bis(2,6-dimethylphenyl)-1,4-diaza-2-(3-trimethylsiloxypropyl)-3-methyl-1,3-butadiene Following the procedure of example 2, [N,N'-bis(2,6-dimethylphenyl)-1,4-diaza-2-(3-trimethylsiloxypropyl)-3-methyl-1,3-butadiene] (L1) was obtained starting from N,N'-bis(2,6-dimethylphenyl)-1,4-diaza-2,3-dimethyl-1,3-butadiene.

$^1$H NMR (C$_6$D$_6$, 298K, 300 MHz): δ 7.03–6.90 (m, 6H, CH$_{Ar}$), 3.32 (t, 2H, CH$_2$—OSiMe$_3$), 2.73–2.67 (m, 2H, CH$_3$—C=NAr), 2.05 and 2.02 (s, 6H each one, o—CH$_3$), 1.99 (s, 3H, CH$_3$—C=NAr), 1.83–1.80 (m, 2H, CH$_2$—CH$_2$—CH$_2$), −0.03 (s, 9H, OSiMe$_3$);

$^{13}$C{$^1$H} NMR (C$_6$D$_6$, 298 K, 75 MHz): δ 170.9 (C=N), 167.4 (C=N), 148.8 Cq$_{(Ar)}$), 148.4 (Cq$_{(Ar)}$), 128.0 (CH$_{Ar}$), 124.5 (Cq$_{(Ar)}$), 123.3 (CH$_{Ar}$), 62.1 (CH$_2$—OSiM$_3$), 30.1 (CH$_2$—CH$_2$—CH$_2$), 25.9 (CH$_2$—C=NAr), 17.8 (o—CH$_3$), 15.9 (CH$_3$—C=NAr), −0.8 (OSiMe$_3$). EI MS, [M]$^+$ m/z 408.

Example 2.2

Synthesis of [N,N'-bis(2,6-diisopropylphenyl)-1,4-diaza-2-(3-trimethylsiloxypropyl)-3-methyl-1,3-butadiene]

Following the procedure of example 2,[N,N'-bis(2,6-diisopropylphenyl)-1,4-diaza-2-(3-trimethylsiloxypropyl)-3-methyl-1,3-butadiene] (L2) was obtained starting from N,N'-bis(2,6-diisopropylphenyl)-1,4-diaza-2,3-dimethyl-1,3-butadiene.

$^1$H NMR (CDCl$_3$, 400 MHz), δ 7.20–7.02 (m, 6H, CH$_{Ar}$), 3.46 (t, 3H, CH$_2$-OSiMe$_3$), 2.73 (m, 4H, CHMe$_2$), 2.55 (m, 2H, CH$_2$—C=NAr), 2.05 (s, 3H, CH$_3$C=N), 1.71 (m, 4H, CH$_2$—CH$_2$—CH$_2$), 1.25–1.10 (m, 24H, CH(CH$_3$)$_2$), −0.05 (s, 9H, OSiMe$_3$);

$^{13}$C{$^1$H} NMR (CDCl$_3$, 298K. 75 MHz): δ 171.1 (C=N), 168.3 (C=N), 146.5 (Cq$_{(Ar)}$), 146.0 (Cq$_{(Ar)}$), 135.5 (Cq$_{(Ar)}$), 135.2 (Cq$_{(Ar)}$), 124.0 (CH$_{Ar}$), 123.9 (CH$_{Ar}$), 123.2 (CH$_{Ar}$), 123.1 (CH$_{Ar}$), 62.9 (CH$_2$—OSiMe$_3$), 29.6 (CH$_2$—CH$_2$—CH$_2$), 28.7 (CHMe$_2$), 26.6 (CH$_2$—C=NAr), 23.5 (CHMe$_2$), 23.0 (CHMe$_2$), 22.5 (CHMe$_2$), 17.5 (CH3—C=NAr), −0.3 (OSiMe$_3$,). The parent molecular ion was observed in EI MS, [M]$^+$ 520.

Example 3

Difunctionalization of Diimine Ligands (General Procedure)

A solution of t-BuLi in pentane (1.7M, 2.4 ml, 4.1 mmol) was added dropwise over a stirred solution of the corresponding N,N'-bis(2,6-dialkylphenyl)-1,4-diaza-2,3-dimethyl-1,3-butadiene (2 mmol) in 20 ml of THF at −80° C. The yellow coloured solution turns bright red. The reaction mixture was then stirred for 0.5 h at −80° C., and for 0.5 h at room temperature, and then ICH$_2$CH$_2$OSiMe$_3$ (1 g, 4.1 mmol) was added. The stirring was continued for 0.5 h, and for 6 h at the room temperature. The solvent was removed under vacuum and the residue extracted with 20 ml of petroleum ether. Filtration and evaporation of the solvent affords the product as yellowish-green oil in ca 90% yields.

Example 3.1

Synthesis of [N,N'-bis(2,6-dimethylphenyl)-1,4-diaza-2,3-di(3-trimethylsiloxypropyl)-1,3-butandiene]

Following the procedure of example 3, [N,N'-bis(2,6-dimethylphenyl)-1,4-diaza-2,3-di(3-trimethylsiloxypropyl)-1,3-butadiene] (L3) was obtained starting from N,N'-bis(2,6-dimethylphenyl)-1,4-diaza-2,3-dimethyl-1,3-butadiene.

$^1$H NMR (C$_6$D$_6$, 400 MHz) δ 7.02 (d, 4H, CH$_{Ar}$), 6.93 (t, 2H, CH$_{Ar}$), 3.35 (t, 4H CH$_2$—OSiMe$_3$), 2.74 (m, 4H, CH$_2$—C=NAr), 2.10 (s, 12H, CH$_3$(ortho)), 1.86 (m, 4H, CH$_2$—CH$_2$—CH$_2$), −0.03 (s, 18H, OSiMe$_3$); $^{13}$C{$^1$H} NMR (C$_6$D$_6$, 100 MHz) δ 170.6 (C=N), 148.5 (Cq$_{(Ar)}$), 128.7 (CH$_{Ar}$), 124.5 (Cq$_{(Ar)}$), 123.2 (CH$_{Ar}$), 62.2 (CH$_2$—OSiMe$_3$), 30.1 (CH$_2$—CH$_2$—CH$_2$), 26.0 (CH$_2$—C=NAr), 18.1 (CH$_3$(ortho)), −0.9 (OSiMe$_3$). The parent molecular ion was observed in EI MS, [M]$^+$ m/z 524.

Example 3.2

Synthesis of [N,N'-bis(2,6-diethylphenyl)-1,4-diaza-2,3-di(3-trimethylsiloxypropyl)-1,3-butadiene]

Following the procedure of example 3, [N,N'-bis(2,6-diethylphenyl)-1,4-diaza-2,3-di(3-trimethylsiloxypropyl)-1,3-butadiene] (L4) was obtained starting from N,N'-bis(2,6-diethylphenyl)-1,4-diaza-2,3-dimethyl-1,3-butadiene.

$^1$H NMR (CDCl$_3$, 300 MHz): δ 7.13–7.06 (m, 6H, CH$_{Ar}$), 3.31 (t, 4H, CH$_2$—OSiMe$_3$), 2.85–2.79 (m, 4H, CH$_2$—C=NAr), 2.63–2.45 (m, 8H, CH$_2$—Me), 1.94–1.87 (m, 4H, CH$_2$—CH$_2$—CH$_2$), 1.24 (q, 12H, CH$_2$—CH$_3$), −0.04 (s, 18H, OSiMe$_3$).

Example 3.3

Synthesis of [N,N'-bis(2,6-diisopropylphenyl)-1,4-diaza-2,3-di(3-trimethylsiloxypropyl)-1,3-butadiene]

Following the procedure of example 3, [N,N'-bis(2,6-diisopropylphenyl)-1,4-diaza-2,3-di(3-trimethylsiloxypropyl)-1,3-butadiene] (L5) was obtained starting from N,N'-bis(2,6-diisopropylphenyl)-1,4-diaza-2,3-dimethyl-1,3-butadiene.

$^1$H NMR (CDCl$_3$, 400 MHz): δ 7.12 (d, 4H, CH$_{Ar}$), 7.05 (t, 2H, CH$_{Ar}$), 3.45 (t, 4H, CH$_2$—OSiMe$_3$), 2.71 (sept, 4H, CHMe$_2$), 2.53–2.47 (m, 4H, CH$_2$—C=NAr), 1.72–1.67 (m, 4H, CH$_2$—CH$_2$—CH$_2$), 1.21 (d, 12H, CHMeMe'), 1.12 (d, 12H, CHMeMe'), −0.04 (s, 18H, OSiMe$_3$); $^{13}$C NMR (CDCl$_3$, 75 MHz) δ 170.8 (C=N), 146.0 (Cq$_{(Ar)}$), 135.3 (Cq$_{(Ar)}$), 123.9 (CH$_{Ar}$), 123.1 (CH$_{Ar}$), 62.9 (CH$_2$—OSiMe$_3$), 29.4 (CH$_2$—CH$_2$—CH$_2$), 28.7 (CHMe$_2$), 26.8 (CH$_2$—C=NAr), 23.6 (CHMeMe'), 22.5 (CHMeMe'), −0.3 (OSiMe$_3$) EI MS, [M'—C$_3$H$_7$] m/z 593.

Example 4

Synthesis of Monofunctionalized Complexes

Example 4.1

Synthesis of (N,N'-bis(2,6-dimethylphenyl)-1,4-diaza-2-(3-trimethylsiloxypropyl)-3-methyl-1,3-butadiene) nickel dibromide (NC1)

A solution of (N,N'-bis(2,6-dimethylphenyl)-1,4-diaza-2-(3-trimethylsiloxypropyl)-3-methyl-1,3-butadiene) (2.2 mmol) in THF was added to a slurry of $NiBr_2(DME)$ (679 mg 2.2 mmol) in 40 ml of cold (−80° C.) THF. The resulting mixture was stirred for 5 h at room temperature, and the solvent evaporated in vacuum. Extraction of the residue with 40 ml of diethyl ether, filtration and addition of 40 ml of petroleum ether causes the precipitation of the complexes, which can be isolated as brown powders in ca. 30% yield.

Example 4.2

Synthesis of (N,N'-bis(2,6-diisopropylphenyl)-1,4-diaza-2-(3-trimethylsiloxypropyl)-3-methyl-1,3-butadiene) nickel dibromide (NC2)

A solution of (N,N'-bis(2,6-diisopropylphenyl)-1,4-diaza-2-(3-trimethylsiloxypropyl)-3-methyl-1,3-butadiene) (2.2 mmol) in THF was added to a slurry of $NiBr_2(DME)$ (679 mg, 2.2 mmol) in 40 ml of cold (−80° C.) THF. The resulting mixture was stirred for 5 h at room temperature, and the solvent evaporated in vacuum. Extraction of the residue with 40 ml of diethyl ether, filtration and addition of 40 ml of petroleum ether causes the precipitation of the complexes, which can be isolated as brown powders in ca. 30% yield.
N,N'-bis(2,6-diisopropylphenyl)-1,4-diaza-2-(3-trimethylsiloxypropyl)-3-methyl-1,3-butadiene) nickel dibromide (recrystallized from CH2Cl2 at −80° C., red-brown needles). Anal. Found: C, 50.24; H, 6.36; N, 3.96. Calc.: C, 53.62; H, 7.04; N, 3.79%. IR (nujol): 1637 (w) (v(C=N)), 1262 (m) and 1252 (m) (δ(Si—CH3)), 1100 (s) and 868 (m) (v(Si—O—C)), 845 (m) (v(Si—C)).

Example 5

Synthesis of Difunctionalized Complexes

Example 5.1

Synthesis of (N,N'-bis(2,6-dimethylphenyl)-1,4-diaza-2,3-di(3-trimethylsiloxypropyl)-1,3-butadiene)nickel dibromide (NC3)

Following the same procedure described in example 4, an equimolecular amount of $NiBr_2(DME)$ and (N,N'-bis(2,6-dimethylphenyl)-1,4-diaza-2,3-di(3-trimethylsiloxypropyl)-1,3-butadiene) were reacted in THF, the solvent removed under vacuum and the residue extracted with diethyl ether. After removing under vacuum the diethyl ether, stirring of the oily residue vigorously with 20 ml of petroleum ether results in the formation of a dark brown solid, which was collected by filtration, washed with 20 ml of petroleum ether and dried under vacuum. The products were obtained in ca. 35% yield.

(N,N'-bis(2,6-dimethylphenyl)-1,4-diaza-2,3-di(3-trimethylsiloxypropyl)-1,3-butadiene)nickel dibromide: IR (nujol): 1627 (w) (v(C=N)), 1251 (s) (δ(Si-CH3)), 1098 (s) and 869 (m) (v(Si—O—C)), 842 (s) (v(Si—C)).

Example 5.2

Synthesis of (N,N'-bis(2,6-diethylphenyl)-1,4-diaza-2,3-di(3-trimethylsiloxypropyl)-1,3-butadiene)nickel dibromide (NC4)

Following the same procedure described in example 5.1, an equimolecular amount of $NiBr_2(DME)$ and (N,N'-bis(2,6-diethylphenyl)-1,4-diaza-2,3-di(3-trimethylsiloxypropyl)-1,3-butadiene) were reacted in THF.

Example 5.3

Synthesis of (N,N'-bis(2,6-diisopropylphenyl)-1,4-diaza-2,3-di(3-trimethylsiloxypropyl)-1,3-butadiene) nickel dibromide (NC5)

Following the same procedure described in example 5.1, an equimolecular amount of $NiBr_2(DME)$ and (N,N'-bis(2,6-diisopropyllphenyl)-1,4-diaza-2,3-di(3-trimethylsiloxypropyl)-1,3-butadiene) were reacted in THF.

Example 6

Preparation of Supported Catalyst Precursors on Calcined Silica

Silica (XPO 2407) supplied by Grace Co. was calcined according to the following procedure:

(1) Warm up from 25 to 400° C. in 2 h (2) Maintain at 400° C. for 6 h (3) Warm up from 400 to 800° C. in 1 h (4) Maintain at 800° C. for 4 h (5) Cool down to room temperature under atmosphere of dry nitrogen To a given amount of the silica thus treated, an amount of the nickel complex prepared according to examples 4 or 5 was added. Toluene was added and the mixture was stirred for a given time (see Table 1) at room temperature and then at 60–70° C. Stirring of the suspension was provided at 500 rpm with a blade stirrer in order not to break-up the silica particles. Then the suspension was filtered and the solid washed with toluene. The solid can be further washed with dichloromethane in order to assure complete removal of non-anchored complex. The solid was then dried under vacuum. Finally the amount of nickel in the solid was determined analytically by ICP.

The results are reported in Table 1

TABLE 1

| | Catalyst Precursors | | | | | | |
|---|---|---|---|---|---|---|---|
| Catalyst Precursor | Nickel Complex | Mg Ni complex | grams of Silica | Time at r.t. | Time at 60–70° C. | Wash ($CH_2Cl_2$) | Percentage of Ni* |
| CP1 | NC2 | 102 | 1.69 | 20 h | None | No | 0.53 ± 0.03 |
| CP2 | NC3 | 56 | 1.50 | 22 h | 22 h | Yes | 0.14 ± 0.01 |
| CP3 | NC3 | 138 | 2.01 | 17 h | 48 h | Yes | 0.75 ± 0.01 |

*Measured by ICP

Example 7

Preparation of Supported Catalytic Systems on Silica-MAO

Catalytic systems were prepared by supporting on silica-MAO according three procedures:

Method A: Inside a dry-box, the solid nickel complexes prepared according to examples 4 or 5, and silica-MAO provided by Witco (TA 02794/HL/04) were mixed together in the amounts shown in Table 2. Then 50 mL of dry toluene were added to the mixtures and stirred at 500 rpm with a blade stirrer. The suspensions, which were bright red coloured at the beginning, turned gradually to a deep-blue coloration. After 20–22 h, stirring was stopped, the mixtures filtered and the solids washed with abundant dry toluene before drying in vacuo.

Method B: Inside a dry-box, 1.78 g of the silica-MAO provided by Witco (TA 02794/HL/04) was added in small portions to 2.5 mL of a ca. 0.065M solution of nickel complex NC3 (totalling ca. 120 mg of complex). The reaction mass was stirred with a spatula after each addition. Finally the thick slurry was dried under vacuum resulting in a free flowing powder.

Method C: Inside a dry-box, a ca. 0.065M solution in toluene of the nickel complex NC3 as added to 1.8 g of silica-MAO provided by Witco (FA 02794/HL/04). Addition was performed in three portions of 1.0 mL, 1.0 mL and 0.5 mL totalling ca. 120 mg of complex. After each addition, the reaction mixture was stirred and mixed up with a spatula. Finally the thick slurry was dried under vacuum resulting in a free flowing powder.

The amounts of supported Ni and Al were analytically measured for each case with Inductively Coupled Plasma Spectrometry (ICP) techniques.

The following heterogeneous catalytic systems were thus prepared (Table 2).

in discrete solid particles, it was recovered by filtration, washed and dried at 10 mm Hg/70° C. for 20 h. When the resultant polymer formed a gel or an amorphous mass, the methanol and heptane phases were separated before removing under vacuum the solvent from the heptane phase. Conditions of the essays and resulting polymer properties are shown in Table 3.

Example 9

Polymerization Employing Catalyst Precursors Supported on Calcined Silica at 4 Bar of Ethylene General Procedure Reactor Volume. 1.3 L; Solvent, n-heptane (600 ml), Co-Catalyst (MAO 10% m toluene from Witco The reactor was filled with the given amount of solvent, degassed and saturated with ethylene at 3.75 bar at the set temperature. Then the co-catalyst was injected into the reactor. For the addition of the solid catalyst precursor from Table 1, the following procedure was followed: In a dry-box, a hollow stainless steel column fitted with a ball valve at each end was filled with the required weight of the solid catalyst and then filled-up with dry heptane. The column was taken outside the dry box with both valves closed and then connected vertical wise to the ethylene line (at the top end) and the reactor system (at the bottom end). The top valve was opened in order to let ethylene in at 4 bar before opening the bottom valve to allow the drop of the catalyst inside the reactor pushed by the ethylene flow. The ethylene gas consumed during polymerization was immediately replaced by free flow from the ethylene line in order to keep a pressure of 4 bar. After the given reaction time, the polymerisation was stopped by, first, fast degassing and depressurisation of the system and, second, by adding the polymerisation mixture to methanol with a few drops of HCl.

TABLE 2

Catalytic systems based on silica MAO

| Catalytic System | Nickel Complex | Method | Grams of Ni Complex | Grams of Silica-MAO | % Ni* | % Al* | Colour |
|---|---|---|---|---|---|---|---|
| CS1 | NC1 | A | 0.224 | 4.0 | 0.57 ± 0.04 | 22.0 ± 0.9 | Blue |
| CS2 | NC2 | A | 0.120 | 1.8 | 0.54 ± 0.02 | 19 ± 1 | Blue |
| CS3 | NC3 | C | 0.120 | 1.8 | 0.29 ± 0.01 | 22 ± 1 | Blue |
| CS4 | NC3 | B | 0.120 | 1.8 | 0.25 ± 0.01 | 23.0 ± 0.3 | Blue |
| CS5 | NC4 | A | 0.190 | 2.5 | 0.53 ± 0.02 | 21.7 ± 0.8 | Blue |
| CS6 | NC5 | A | 0.212 | 3.0 | 0.37 ± 0.02 | 19.5 ± 0.4 | Blue |

*Measured by ICP

Example 8

Polymerisation Employing Non-Supported Catalyst Systems

General Procedure.

Reactor Volume: 1.3 L; Solvent: n-heptane (600 ml); Co-Catalyst: MAO 10% in toluene from Witco. The reactor was filled with the solvent, degassed and saturated with ethylene at 4.0 bar at the set temperature. Then first the co-catalyst and second the nickel complex prepared according Examples 4 or 5 dissolved in dichloromethane were injected into the reactor. The ethylene gas consumed during polymerisation was immediately replaced by free flow from the ethylene line in order to keep a pressure of 4 bar. After the given reaction time, the polymerisation was stopped by, first, fast degassing and depressurisation of the system and, second, by adding the polymerisation mixture to methanol with a few drops of HCl. In cases when the polymer resulted The polymer was recovered by filtration, washed and dried at 10 mm Hg/70° C. for 20 h. The conditions and resulting polymer characteristics are shown in Table 4.

Example 10

Polymerisation Employing Catalyst Precursors Supported on Calcined Silica Performed at Pressures Higher than 4 Bar General Procedure.

Reactor Volume: 1 L; Solvent: isobutane (500 ml); Co-Catalyst: MAO 10% in toluene from Witco.

A stainless steel reactor was used. The co-catalyst was injected into the reactor. Then it was filled with the isobutane and saturated with ethylene at the set temperature and pressures. For the addition of the catalyst precursor from Table 1, a similar procedure as the one employed in Example 9 was followed. After the given reaction time, the polymerisation was stopped by, first, fast degassing and depressurisation of the system and, second, by adding the polymerisation mixture to methanol with a few drops of HCl. The polymer was recovered by filtration, washed and dried at 10 mm Hg/70° C. for 20 h. The conditions and resulting polymer characteristics are shown in Table 4.

Example 11

Polymerization Employing Catalyst Systems Supported on Silica-MAO Performed at 4 Bar of Ethylene:

Reactor Volume: 1.3 L; Solvent: n-heptane (600 mL). The reactor was filled with the solvent degassed and saturated with ethylene at 3.75 bar at the set temperature. Then a volume of a heptane solution of triisobutylaluminium (TIBA), was injected into the reactor. This alkylaluminium is thought to act as scavenger of possible impurities. It was found that the absence of it resulted in diminished activities.

For the addition of the supported catalyst from Table 2, the following procedure was followed: In a dry-box, a hollow stainless steel column fitted with a ball valve at each end was filled with the required weight of the solid catalyst and then filled-up with dry heptane. The column was taken outside the dry box with both valves closed and then connected vertical wise to the ethylene line (at the top end) and the reactor system (at the bottom end). The top valve was opened in order to let ethylene in at 4 bar before opening the bottom valve to allow the drop of the catalyst inside the reactor pushed by the ethylene flow. The ethylene gas consumed during polymerisation was immediately replaced by free flow from the ethylene line in order to keep a pressure of 4 bar. After the given reaction time, the polymerisation was stopped by, first, fast degassing and depressurisation of the system and, second, by adding the polymerisation mixture to methanol with a few drops of HCl. The polymer was recovered by filtration, washed and dried at 10 mm Hg/70° C. for 20 h. Conditions of the essays and resulting polymer properties are shown in Table 5.

Example 12

Polymerisation Essays Employing Catalyst Systems Supported on Silica-MAO Performed at Pressures Higher than 4 Bar of Ethylene:

Reactor Volume: 1 L; Solvent: isobutane (500 mL at ca. 20 bar). A stainless steel reactor was used. A volume of a heptane solution of triisobutylaluminium (TIBA) was injected into the reactor. This alkylaluminium is thought to act as scavenger of impurities. Then it was filled with the isobutane and saturated with ethylene at the set temperature and pressures. For the addition of the solid catalyst systems from Table 7, a steel hollow column with two valves was used in a similar way as the one employed at 4 bar in example 11. After the given reaction time, the polymerisation was stopped by, first, fast degassing and depressurisation of the system and, second, by adding the polymerisation mixture to methanol with a few drops of HCl. The polymer was recovered by filtration, washed and dried at 10 mm Hg/70° C. for 20 h. Conditions of the essays and resulting polymer properties are shown in Table 5.

TABLE 3

Ethylene Polymerisation Essays employing non-supported catalyst systems

| Essay | Metal Complex | mmol Ni | Co-Catalyst | Al/Ni | P (bar)[1] | T (° C.) | t (min) | g PE | Activity[2] | Mn | Total Branches[3] | Me[3] | Hex+[3] |
|---|---|---|---|---|---|---|---|---|---|---|---|---|---|
| S1 | NC1 | 0,0019 | MAO | 870 | 4 | 45 | 15 | 31.8 | 1,67E + 07 | 121.700 | 15.2 | 12.6 | 1.2 |
| S2 | NC1 | 0.0019 | MAO | 870 | 4 | 60 | 15 | 18.9 | 9.95E + 06 | 54.500 | 38.7 | 27.5 | 6.0 |
| S3 | NC1 | 0.0019 | MAO | 870 | 4 | 80 | 15 | 5.9 | 3.11E + 06 | 23.700 | 70.0 | 47.9 | 11.1 |
| S4 | NC2 | 0.0034 | MAO | 735 | 4 | 45 | 15 | 6.93 | 2,04E + 06 | — | 89.4 | 72.5 | 7.67 |
| S5 | NC2 | 0.0034 | MAO | 1470 | 4 | 45 | 15 | 7.11 | 2,09E + 06 | — | 80.8 | 65.9 | 7.80 |
| S6 | NC2 | 0.0067 | MAO | 735 | 4 | 45 | 15 | 12.14 | 1.81E + 06 | 255.400 | 85.5 | 67.1 | 10.86 |
| S7 | NC2 | 0.0067 | MAO | 368 | 4 | 45 | 15 | 11.22 | 1.67E + 06 | 316.300 | 89.7 | 72.5 | 8.72 |
| S8 | NC3 | 0.0016 | MAO | 768 | 4 | 45 | 15 | 15.15 | 9.47E + 06 | 160.100 | 7.4 | 7.4 | 0.00 |
| S9 | NC3 | 0.0016 | MAO | 768 | 4 | 60 | 15 | 14.11 | 8.82E + 06 | 86.200 | 26.8 | 21.7 | 2.24 |
| S10 | NC3 | 0.0016 | MAO | 768 | 4 | 70 | 15 | 10.95 | 6.84E + 06 | 57.500 | 38.9 | 28.5 | 1.59 |
| S11 | NC4 | 0.0006 | MAO | 1320 | 4 | 45 | 30 | 9,28 | 7,73E + 06 | 388.800 | 37.0 | 28.2 | 2.55 |
| S12 | NC4 | 0.0006 | MAO | 1320 | 4 | 60 | 30 | 9.08 | 7.57E + 06 | 144.100 | 56.9 | 40.1 | 8.26 |
| S13 | NC4 | 0.0006 | MAO | 1320 | 4 | 80 | 30 | 5.85 | 4.88E + 06 | 91.700 | 74.2 | 55.0 | 8.49 |
| S14 | NC5 | 0.0031 | MAO | 836 | 4 | 45 | 15 | 7.26 | 2.34E + 06 | 416.100 | 64.0 | 50.5 | 7.83 |
| S15 | NC5 | 0.0031 | MAO | 836 | 4 | 60 | 15 | 3.93 | 1.27E + 06 | 312.500 | 81.3 | 56.6 | 12.50 |

[1]Approximate ethylene partial pressure.
[2]Activity measured in g PE/(mol Ni · bar · h).
[3]As measured by $^{13}$C-NMR in number of branches per 1000 C; Me = methyl branches; Hex+ = hexyl or longer branches

TABLE 4

Ethylene Polymerisation Essays in Slurry employing catalyst precursors supported on calcined silica

| Essay | Catalyst Precursor | mmol Ni | Co-Catalyst | Al/Ni | P (bar)[1] | T (° C.) | t (min) | g PE | Activity[2] | Mn | Total Branches[3] | Me[3] | Hex+[3] |
|---|---|---|---|---|---|---|---|---|---|---|---|---|---|
| E1 | CP1 | 0.0135 | MAO | 343 | 4 | 45 | 30 | 13.21 | 4.89E + 05 | 261.100 | 88.47 | 66.29 | 7.48 |
| E2 | CP2 | 0.0023 | MAO | 3321 | 4 | 45 | 30 | 0.96 | 2.09E + 05 | — | 19.57 | 19.57 | 0.00 |
| E3 | CP3 | 0.0128 | MAO | 599 | 4 | 45 | 60 | 1.54 | 3.01E + 04 | 113.600 | 8.97 | 7.27 | 0.57 |
| E4 | CP3 | 0.0141 | MAO | 797 | 10 | 60 | 60 | 1.61 | 1.14E + 04 | — | 0.00 | 0.00 | 0.00 |
| E5 | CP3 | 0.0141 | MAO | 797 | 27 | 60 | 60 | 1.42 | 3.73E + 03 | — | 2.48 | 2.48 | 0.00 |

[1]Approximate ethylene partial pressure.
[2]Activity measured in g PE/(mol Ni · bar · h).
[3]As measured by $^{13}$C-NMR in number of branches per 1000 C; Me = methyl branches; Hex+ = hexyl or longer branches

TABLE 5

Polymerization essays employing catalyst systems supported on silica-MAO

| Essay | Catalyst System | Nickel Complex | Ni (mmol) | Alkyl Aluminium | Al/Ni[1] | p[2] (bar) | T (°C.) | t (min) | g PE | Activity[3] | Mn | Total[4] Branches | Me[4] | Et[4] | Bu[4] | Pen[4] | Hex+[4] |
|---|---|---|---|---|---|---|---|---|---|---|---|---|---|---|---|---|
| F1 | CS1 | NC1 | 0,0049 | TIBA | 185 | 4 | 45 | 30 | 9.81 | 1.01E+06 | 133.800 | 12.02 | 12.02 | 0.00 | 0.00 | 0.00 | 0.00 |
| F2 | CS1 | NC1 | 0,0049 | TIBA | 185 | 4 | 60 | 30 | 6.36 | 6.55E+05 | 93.300 | 23.43 | 19.40 | 1.98 | 0.58 | 0.00 | 1,47 |
| F3 | CS1 | NC1 | 0,0049 | TIBA | 185 | 4 | 80 | 30 | 5.95 | 6.13E+05 | 27.400 | 49.10 | 34.98 | 4.49 | 2.55 | 1.97 | 5,11 |
| F4 | CS1 | NC1 | 0,0120 | TIBA | 400 | 27 | 80 | 60 | 37.5 | 1.15E+05 | — | 10.55 | 9.11 | 1.11 | 0.00 | 0.00 | 0,33 |
| F5 | CS1 | NC1 | 0,0120 | TIBA | 401 | 27 | 90 | 60 | 17.5 | 5.38E+04 | 45.000 | 21.01 | 17.36 | 1.45 | 0.92 | 0.00 | 1,28 |
| F6 | CS1 | NC1 | 0,0120 | TIBA | 400 | 27 | 100 | 60 | 12.6 | 3.88E+04 | 44.100 | 27.88 | 22.17 | 1.77 | 1.11 | 1.04 | 1,79 |
| F7 | CS2 | NC2 | 0,0046 | TIBA | 583 | 4 | 45 | 15 | 1.4 | 3.04E+05 | 354.000 | 44.65 | 39.66 | 2.22 | 0.00 | 1.11 | 1,66 |
| F8 | CS2 | NC2 | 0,0120 | TIBA | 398 | 27 | 80 | 60 | 20.2 | 6.25E+04 | 374.000 | 39.35 | 35.81 | 0.86 | 0.00 | 0.53 | 2,15 |
| F9 | CS2 | NC2 | 0,0120 | TIBA | 398 | 27 | 90 | 60 | 9.39 | 2.91E+04 | 303.200 | 57.75 | 47.17 | 3.05 | 1.55 | 1.36 | 4,62 |
| F10 | CS2 | NC2 | 0,0120 | TIBA | 398 | 27 | 100 | 60 | 7.03 | 2.18E+04 | 252.800 | 65.60 | 54.81 | 3.95 | 0.77 | 0.95 | 5,12 |
| F11 | CS3 | NC3 | 0,0027 | TIBA | 193 | 4 | 45 | 15 | 2.2 | 8.05E+05 | 155.300 | 11.87 | 10.77 | 1.10 | 0.00 | 0.00 | 0,00 |
| F12 | CS3 | NC3 | 0,0027 | TIBA | 194 | 4 | 60 | 15 | 1.9 | 6.99E+05 | 104.200 | 18.88 | 17.53 | 1.35 | 0.00 | 0.00 | 0,00 |
| F13 | CS3 | NC3 | 0,0055 | TIBA | 193 | 4 | 70 | 15 | 3.96 | 7.24E+05 | 66.600 | 28.88 | 24.07 | 2.46 | 0.68 | 0.00 | 1,67 |
| F14 | CS3 | NC3 | 0,0054 | TIBA | 194 | 4 | 80 | 15 | 3.06 | 5.63E+05 | 42.700 | 42.17 | 33.54 | 2.31 | 1.47 | 0.75 | 2,90 |
| F15 | CS4 | NC3 | 0,0139 | TIBA | 404 | 27 | 80 | 60 | 74.4 | 1.98E+05 | 125.700 | 8.34 | 8.34 | 0.00 | 0.00 | 0.00 | 0,00 |
| F16 | CS4 | NC3 | 0,0139 | TIBA | 404 | 27 | 90 | 60 | 40.2 | 1.07E+05 | 104.000 | 10.31 | 10.31 | 0.00 | 0.00 | 0.00 | 0,00 |
| F17 | CS4 | NC4 | 0,0042 | TIBA | 401 | 27 | 100 | 60 | 8.74 | 7.62E+05 | 87.800 | 18.90 | 17.77 | 1.13 | 0.00 | 0.00 | 0,00 |
| F18 | CS5 | NC4 | 0,0045 | TIBA | 443 | 27 | 45 | 30 | 5.21 | 5.77E+05 | 299.500 | 22.25 | 20.06 | 1.68 | 0.00 | 0.00 | 0,51 |
| F19 | CS5 | NC4 | 0,0045 | TIBA | 443 | 4 | 60 | 30 | 2.8 | 3.10E+05 | 188.300 | 37.90 | 30.20 | 2.99 | 1.64 | 0.00 | 3,07 |
| F20 | CS5 | NC4 | 0,0045 | TIBA | 443 | 4 | 80 | 30 | 1.01 | 1.12E+05 | 76.700 | 64.09 | 48.22 | 3.94 | 3.04 | 3.30 | 5,59 |
| F21 | CS5 | NC4 | 0,0117 | TIBA | 400 | 27 | 80 | 60 | 33.5 | 1.06E+05 | 112.700 | 21.08 | 16.68 | 4.40 | 0.00 | 0.00 | 0,00 |
| F22 | CS5 | NC4 | 0,0117 | TIBA | 400 | 27 | 90 | 60 | 18.9 | 5.96E+04 | 135.900 | 30.71 | 25.18 | 2.72 | 0.00 | 0.48 | 2,33 |
| F23 | CS6 | NC5 | 0,0095 | TIBA | 424 | 4 | 45 | 15 | 2.7 | 2.86E+05 | 549.600 | 52.48 | 40.54 | 4.22 | 0.00 | 0.00 | 7,72 |
| F24 | CS6 | NC5 | 0,0032 | TIBA | 668 | 4 | 60 | 15 | 0.51 | 1.62E+05 | 228.500 | 56.72 | 42.70 | 3.38 | 0.00 | 0.00 | 10,64 |
| F25 | CS6 | NC5 | 0,0063 | TIBA | 477 | 4 | 80 | 15 | 0.66 | 1.05E+05 | 110.900 | 71.05 | 50.39 | 4.94 | 4.76 | 0.00 | 10,96 |
| F26 | CS6 | NC5 | 0,0120 | TIBA | 397 | 27 | 80 | 60 | 8.63 | 2.67E+04 | 175.700 | 32.70 | 29.98 | 1.41 | 0.00 | 0.00 | 2,01 |
| F27 | CS6 | NC5 | 0,0120 | TIBA | 400 | 27 | 90 | 60 | 4.02 | 1.24E+04 | 240.200 | 43.70 | 38.74 | 1.47 | 0.00 | 0.00 | 3,49 |
| F28 | CS6 | NC5 | 0,0120 | TIBA | 400 | 27 | 100 | 60 | 2.64 | 8.17E+03 | 157.600 | 53.08 | 46.32 | 1.71 | 0.40 | 0.78 | 3,87 |

[1]Al added as TIBA;
[2]Approximate partial pressure of ethylene;
[3]Activity measured in in g PE/(mol Ni · bar · h);
[4]As measured by 13C NMR in numebr of branches per 1000 C; Me = methyl branches; Et = Ethyl branches; Bu = butyl branches; Pen = pentyl branches; Hex+ = hexyl or longer branches

What is claimed is:

1. A composition comprising a porous inorganic solid and a nickel or palladium complex of a bidentate diimino ligand containing at least one group $OSi(R)_3$ wherein each R, equal to or different from each other, is selected from the group consisting of: $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl, and $C_8$–$C_{20}$ alkenylaryl.

2. A composition according to claim 1 wherein the complex is represented by the following formula:

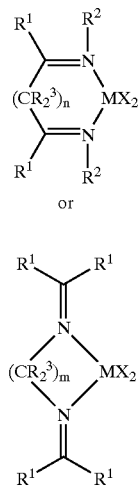

wherein:

M is nickel or palladium; n is 0, 1, 2, or 3; m is 1, 2, or 3;

each X, equal to or different from each other, is selected from a group consisting of: halogen, hydrogen, OR, $N(R)_2$, and R; wherein two X's taken together can also form an aromatic or aliphatic divalent ligand containing two equal or different donor atoms belonging to groups 14–16 of the periodic table of the elements;

each $R^1$, equal or different from each other, is selected from the group consisting of: hydrogen, a monovalent aliphatic hydrocarbon group, and a monovalent aromatic hydrocarbon group, each hydrocarbon group optionally containing heteroatoms of groups 14 to 16 of the periodic table of the elements or boron; with the proviso that at least one $R^1$ group is represented by the formula:

$R^4OSi(R^7)_3$;

wherein:

each $R^7$, equal to or different from each other, is selected from the group consisting of: $C_1$–$C_{20}$ alkyl, $C_3$–$C_{20}$ cycloalkyl, $C_6$–$C_{20}$ aryl, $C_2$–$C_{20}$ alkenyl, $C_2$–$C_{20}$ arylalkyl, $C_7$–$C_{20}$ alkylaryl, $C_8$–$C_{20}$ arylalkenyl, and $C_8$–$C_{20}$ alkenylaryl;

each $R^4$, equal to or different from each other, is a divalent aliphatic or aromatic hydrocarbon group containing from 1 to 20 carbon atoms, optionally containing from 1 to 5 heteroatoms of groups 14 to 16 of the periodic table of the elements and boron;

each $R^2$, equal to or different from each other, is a radical which contains, from 1 to 20 carbon atoms; $R^2$ optionally contains heteroatoms of groups 14 to 16 of the periodic table of the elements and/or boron;

each $R^3$, equal to or different from each other, is hydrogen or a radical which contains from 1 to 20 carbon atoms; $R^3$ optionally contains heteroatoms of groups 14 to 16 of the periodic table of the elements and/or boron;

two or more of $R^1$, $R^2$, $R^3$, and $R^4$ can also unite to form a from 4 to 15 membered aliphatic or aromatic ring, the ring optionally containing heteroatomns of groups 14 to 16 of the periodic table of the elements and/or boron.

3. A composition according to claim 2, wherein $R^4$ is represented by the formula $CR^5_2(R^6)_aCR^5_2$ wherein:

each $R^5$, equal to or different from each other, is selected from the group consisting of: hydrogen, $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl, and $C_8$–$C_{20}$ alkenylaryl; two $R^5$ can also unite to form a ring;

$R^6$ is a divalent radical selected from the group consisting of: O, NR, S, $SiR^5_2$, $C_1$–$C_{20}$ alkylidene, $C_3$–$C_{20}$ cycloalkylidene, $C_2$–$C_{20}$ alkenylidene, $C_6$–$C_{20}$ arylidene, $C_7$–$C_{20}$ alkylarylidene, $C_7$–$C_{20}$ arylalkylidene, $C_8$–$C_{20}$ arylalkenylidene, and $C_8$–$C_{20}$ alkenylarylidene, optionally containing heteroatoms of groups 14 to 16 of the periodic table of the elements and/or boron; and a is 0 or 1.

4. A composition according to claim 3, wherein the $R^1$ group represented by the formula $R^4OSi(R^7)_3$ is selected from the group consisting of:

—$CH_2$—$CH_2$—$OSiMe_3$; —$CH_2$ $(CH_2)_p$—$CH_2OSiMe_3$ wherein p ranges from 1 to 10;

—$CH_2$—O—$CH_2$—$OSiMe_3$; —$CH_2$—$C_6H_4$—$CH_2$—$OSiMe_3$; —$CH(Et)$—$CH_2$—$OSi(Et)_2Me$;

—$CH_2$—$CH_2$—O—$CH_2OSi(iPr)_3$; —$CH_2$—$Si(CH_3)_2$—$CH_2OSi(iPr)_3$;

—$CH_2$—$CH_2$—$Si(CH_3)_2$—$CH_2OSi(iPr)_3$;

—$CH_2$—$CH_2$—$CH_2$—$N(CH_3)$—$CH_2$—$CH_2$—$CH_2OSi(iPr)_3$;

—$C(Me)_2$—$CH_2$—$C_6H_4$—$CH_2$—$CH_2$—$OSi(C_5H_{11})_3$;

—$CH_2$—$CH_2$—$C_6H_4$—$C_6H_4$—O—$CH_2$ $CH_2$ $OSi(CH_2Ph)_3$; and

—$C(CH_3)_2$—$C(CH_3)_2$—$OSi(C_6H_4Me)_3$; —$CH(Me)$—$CH(Me)$—$OSi(Et)(Me)_2$.

5. A composition according to claim 2 wherein in formula I or II:

each $R^1$ is independently hydrogen, $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl, or $C_8$–$C_{20}$ alkenylaryl, wherein each hydrocarbyl group is linear or branched, and wherein each hydrocarbyl group is optionally substituted by $BR^5_2$, $OR^5$, $SiR^5_3$, $NR^5_2$, or $R^4OSi(R^7)_3$;

each $R^2$ is independently $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl, or $C_8$–$C_{20}$ alkenylaryl, wherein each hydrocarbyl group is linear or branched, and wherein each hydrocarbyl group is optionally substituted by $BR^5_2$, $OR^5$, $SiR^5_3$, or $NR^5_2$;

each $R^3$ is independently hydrogen, $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl, or $C_8$–$C_{20}$ alkenylaryl, wherein each hydrocarbyl group is linear or branched, and wherein each hydrocarbyl group is optionally substituted by $BR^5_2$, $OR^5$, $SiR^5_3$, or $NR^5_2$;

each $R^5$, equal to or different from each other, is selected from the group consisting of: hydrogen, $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl, and $C_8$–$C_{20}$ alkenylaryl; and two $R^5$ can also unite to form a ring.

6. A composition according to claim 3 wherein the complex is represented by the following formula:

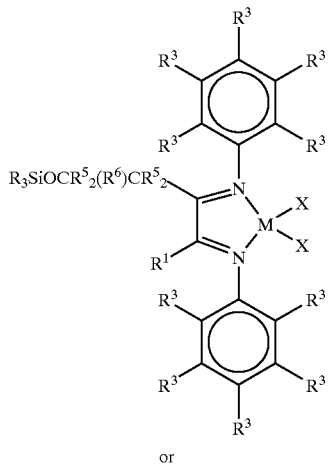

or

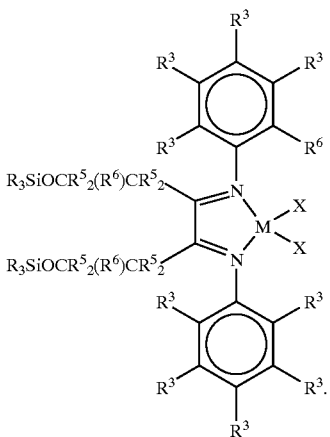

7. The composition of claim 1 wherein the porous inorganic solid is selected from the group consisting of: silica, alumina, silica-alumina, aluminium phosphates, and mixtures thereof.

8. The composition of claim 7 wherein the porous inorganic solid is calcined silica.

9. The composition of claim 7 wherein the porous inorganic solid is silica previously treated with alumoxane.

10. A process for preparing a catalyst component comprising the following steps;

(a) reacting, under anhydrous conditions and an inert atmosphere, a solution comprising at least one complex of a bidentate diimino ligand with a support material at a temperature between −20° C. and 90° C. to yield a product;

(b) filtering and washing the product of step (a) with a solvent, wherein the solvent is an aliphatic or aromatic hydrocarbon or a mixture thereof;

wherein the complex is represented by the formula:

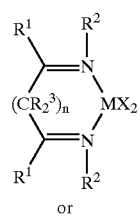

I or

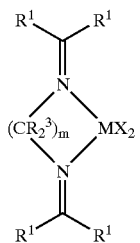

II wherein:

M is nickel or palladium; n is 0, 1, 2, or 3; m is 1, 2, or 3;

each X, equal to or different from each other, is selected from a group consisting of: halogen, hydrogen, OR, $N(R_2)$, and R; wherein R is selected from the group consisting of: $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl, and $C_8$–$C_{20}$ alkenylaryl; wherein two X's taken together can also form an aromatic or aliphatic divalent ligand containing two equal or different donor atoms belonging to groups 14 16 of the periodic table of the elements;

each $R^1$, equal to or different from each other, is selected from the group consisting of: hydrogen, a monovalent aliphatic hydrocarbon group, and a monovalent aromatic hydrocarbon group, each hydrocarbon group optionally containing heteroatoms of groups 14 to 16 of the periodic table of the elements or boron; with the proviso that at least one $R^1$ group is represented by the formula $R^4OSi(R^7)_3$;

wherein:

each $R^7$, equal to or different trait each other, is selected from the group consisting of: $C_1$–$C_{20}$ alkyl, $C_3$–$C_{20}$ cycloalkyl, $C_6$–$C_{20}$ aryl, $C_2$–$C_{20}$ alkenyl, $C_7$–$C_{20}$ arylalkyl, $C_7$–$C_{20}$ alkylaryl, $C_8$–$C_{20}$ arylalkenyl, and $C_8$–$C_{20}$ alkenylaryl;

each $R^4$, equal to different from each other, is a divalent aliphatic or aromatic hydrocarbon group containing from 1 to 10 carbon atoms, optionally containing from 1 to 5 heteroatoms of groups 14 to 16 of the periodic table of the elements and boron;

each $R^2$, equal to or different from each other, is a radical which contains from 1 to 20 carbon atoms; $R^2$ optionally contains heteroatoms of groups 14 to 16 of the periodic table of the elements and/or boron;

each $R^3$, equal to or different from each other, is hydrogen or a radical which contains from 1 to 20 carbon atoms; $R^3$ optionally contains heteroatoms of groups 14 to 16 of the periodic table of elements and/or boron;

two or more $R^1$, $R^2$, $R^3$, and $R^4$ can also unite to form a from 4 to 15 membered aliphatic or aromatic ring, the ring optionally containing heteroatoms of groups 14 to 16 of the periodic table of the elements and/or boron.

11. A polymerization catalyst comprising a cocatalyst and a nickel or palladium complex of a bidentate diimino ligand containing at least one group $OSi(R)_3$ wherein each R, equal to or different, from each other, is selected from the group consisting of: $C_1$-$C_{20}$ alkyl, $C_3$-$C_{20}$ cycloalkyl, $C_6$-$C_{20}$ aryl, $C_2$-$C_{20}$ alkenyl, $C_7$-$C_{20}$ arylalkyl, $C_7$-$C_{20}$ alkylaryl, $C_8$-$C_{20}$ arylalkenyl, and $C_8$-$C_{20}$ alkenylaryl.

12. The polymerization catalyst of claim 11, wherein the cocatalyst comprises an aluminoxane, a boron compound, or a mixture thereof.

13. The polymerization catalyst of claim 11 further comprising an inorganic porous support.

14. The polymerization catalyst of claim 13 wherein the support comprises silica, alumina, silica-alumina, one or more aluminium phosphates, or a mixture thereof.

15. The polymerization catalyst of claim 14 wherein the support is calcined silica.

* * * * *